United States Patent
Connor et al.

(10) Patent No.: US 8,204,174 B2
(45) Date of Patent: Jun. 19, 2012

(54) SYSTEMS AND METHODS FOR DETECTING AN IMAGE OF AN OBJECT BY USE OF X-RAY BEAMS GENERATED BY MULTIPLE SMALL AREA SOURCES AND BY USE OF FACING SIDES OF ADJACENT MONOCHROMATOR CRYSTALS

(75) Inventors: Dean Connor, Brooklyn, NY (US); Christopher Parham, Raleigh, NC (US); Etta Pisano, Chapel Hill, NC (US); Waldo S. Hinshaw, Burlingame, CA (US); Zhong Zhong, Stony Brook, NY (US); Brian P. Wilfley, Los Altos, CA (US)

(73) Assignee: Nextray, Inc., Chapel Hill, NC (US)

( * ) Notice: Subject to any disclaimer, the term of this patent is extended or adjusted under 35 U.S.C. 154(b) by 353 days.

(21) Appl. No.: 12/708,579

(22) Filed: Feb. 19, 2010

(65) Prior Publication Data
US 2010/0310046 A1    Dec. 9, 2010

Related U.S. Application Data

(60) Provisional application No. 61/183,988, filed on Jun. 4, 2009, provisional application No. 61/183,989, filed on Jun. 4, 2009.

(51) Int. Cl.
*G01N 23/087* (2006.01)
*G01N 23/20* (2006.01)
*G01N 23/207* (2006.01)
*G21K 1/06* (2006.01)

(52) U.S. Cl. .................. 378/62; 378/71; 378/84; 378/85

(58) Field of Classification Search ................. 378/62, 378/71, 84, 85
See application file for complete search history.

(56) References Cited

U.S. PATENT DOCUMENTS
3,598,471 A    8/1971    Baldwin et al.
(Continued)

FOREIGN PATENT DOCUMENTS
WO    WO 02/12871 A1    2/2002
(Continued)

OTHER PUBLICATIONS

Notification of Transmittal of the International Search Report and the Written Opinion of the International Searching Authority, or the Declaration for related PCT International Application No. PCT/US2010/037276 to Nextray, Inc.
(Continued)

*Primary Examiner* — Allen C. Ho
(74) *Attorney, Agent, or Firm* — Olive Law Group, PLLC

(57) ABSTRACT

Systems and methods for detecting an image of an object by use of X-ray beams generated by multiple small area sources are disclosed. A plurality of monochromator crystals may be positioned to intercept the plurality of first X-ray beams such that a plurality of second X-ray beams each having predetermined energy levels is produced. Further, an object to be imaged may be positioned in paths of the second x-ray beams for transmission of the second X-ray beams through the object and emitting from the object a plurality of transmission X-ray beams. The X-ray beams may be directed at angles of incidence upon a plurality of analyzer crystals for detecting an image of the object.

123 Claims, 15 Drawing Sheets

U.S. PATENT DOCUMENTS

| | | | | |
|---|---|---|---|---|
| 3,639,039 | A | 2/1972 | Rhodes, Jr. | |
| 3,801,785 | A | 4/1974 | Barrett | |
| 3,882,310 | A | 5/1975 | Barrett | |
| 3,925,660 | A | 12/1975 | Albert | |
| 3,993,398 | A | 11/1976 | Noguchi et al. | |
| 4,007,375 | A | 2/1977 | Albert | |
| 4,284,844 | A | 8/1981 | Belles | |
| 4,310,227 | A | 1/1982 | Zinchuk | |
| 4,517,599 | A | 5/1985 | Zwirn et al. | |
| 4,532,548 | A | 7/1985 | Zwirn et al. | |
| 4,647,154 | A | 3/1987 | Birhbach et al. | |
| 4,718,075 | A | 1/1988 | Horn | |
| 4,882,619 | A | 11/1989 | Hasegawn et al. | |
| 5,008,908 | A | 4/1991 | Jach et al. | |
| 5,123,036 | A | 6/1992 | Uno et al. | |
| 5,127,028 | A | 6/1992 | Wittry | |
| 5,164,975 | A | 11/1992 | Steinmeyer | |
| 5,173,930 | A * | 12/1992 | Hoover | 378/85 |
| 5,195,115 | A | 3/1993 | Schiller et al. | |
| 5,237,598 | A | 8/1993 | Albert | |
| 5,245,648 | A | 9/1993 | Kinney et al. | |
| 5,259,013 | A | 11/1993 | Kuriyama et al. | |
| 5,319,694 | A | 6/1994 | Ingal et al. | |
| 5,339,305 | A | 8/1994 | Curtis et al. | |
| 5,347,400 | A | 9/1994 | Hunter | |
| 5,406,609 | A | 4/1995 | Arai et al. | |
| 5,428,657 | A | 6/1995 | Papanicolopoulos et al. | |
| 5,430,807 | A | 7/1995 | Gravely | |
| 5,457,726 | A | 10/1995 | Miyazaki | |
| 5,457,727 | A | 10/1995 | Frijlink | |
| 5,532,814 | A | 7/1996 | Cha | |
| 5,535,291 | A | 7/1996 | Spencer et al. | |
| 5,541,026 | A | 7/1996 | Matsumoto | |
| 5,579,363 | A | 11/1996 | Ingal et al. | |
| 5,596,620 | A | 1/1997 | Canistraro et al. | |
| 5,634,669 | A | 6/1997 | Colgate, Jr. | |
| 5,635,720 | A | 6/1997 | Mooney et al. | |
| 5,667,736 | A | 9/1997 | Chien | |
| 5,682,412 | A | 10/1997 | Skillicorn et al. | |
| 5,715,291 | A | 2/1998 | Momose | |
| 5,717,733 | A | 2/1998 | Kurbatov et al. | |
| 5,787,146 | A | 7/1998 | Giebeler | |
| 5,801,889 | A | 9/1998 | Meyers et al. | |
| 5,802,137 | A | 9/1998 | Wilkins | |
| 5,805,342 | A | 9/1998 | Gravely | |
| 5,805,662 | A | 9/1998 | Kurbatov et al. | |
| 5,835,561 | A | 11/1998 | Moorman et al. | |
| 5,850,425 | A | 12/1998 | Wilkins | |
| 5,867,264 | A | 2/1999 | Hinnrichs | |
| 5,923,720 | A | 7/1999 | Barton et al. | |
| 5,933,277 | A | 8/1999 | Troxell et al. | |
| 5,949,847 | A | 9/1999 | Terada et al. | |
| 5,953,161 | A | 9/1999 | Troxell et al. | |
| 5,969,864 | A | 10/1999 | Chen et al. | |
| 5,974,211 | A | 10/1999 | Slater | |
| 5,987,095 | A | 11/1999 | Chapman et al. | |
| 6,038,285 | A | 3/2000 | Zhong et al. | |
| 6,041,098 | A | 3/2000 | Touryanski et al. | |
| 6,049,588 | A * | 4/2000 | Cash, Jr. | 378/85 |
| 6,086,708 | A | 7/2000 | Colgate, Jr. | |
| 6,088,425 | A | 7/2000 | Ono | |
| 6,100,978 | A | 8/2000 | Naulleau et al. | |
| 6,125,167 | A * | 9/2000 | Morgan | 378/124 |
| 6,163,593 | A | 12/2000 | Koller et al. | |
| 6,221,579 | B1 | 4/2001 | Everhart et al. | |
| 6,226,349 | B1 | 5/2001 | Schuster et al. | |
| 6,229,870 | B1 * | 5/2001 | Morgan | 378/9 |
| 6,269,144 | B1 | 7/2001 | Dube et al. | |
| 6,320,648 | B1 | 11/2001 | Brueck et al. | |
| 6,333,968 | B1 * | 12/2001 | Whitlock et al. | 378/136 |
| 6,349,004 | B1 | 2/2002 | Fisher et al. | |
| 6,353,656 | B1 | 3/2002 | LeVert et al. | |
| 6,385,289 | B1 | 5/2002 | Kikuchi | |
| 6,399,295 | B1 | 6/2002 | Kaylor et al. | |
| 6,411,367 | B1 | 6/2002 | Baker et al. | |
| 6,517,490 | B1 | 2/2003 | Garlick | |
| 6,525,806 | B1 | 2/2003 | Smith | |
| 6,553,096 | B1 * | 4/2003 | Zhou et al. | 378/122 |
| 6,573,040 | B2 | 6/2003 | Everhart et al. | |
| 6,577,708 | B2 | 6/2003 | Chapman et al. | |
| 6,674,837 | B1 * | 1/2004 | Taskar et al. | 378/122 |
| 6,685,641 | B2 | 2/2004 | Liu | |
| 6,754,307 | B2 | 6/2004 | Brendler et al. | |
| 6,757,104 | B2 | 6/2004 | Nakai | |
| 6,760,399 | B2 | 7/2004 | Malamud | |
| 6,804,324 | B2 | 10/2004 | Martynov et al. | |
| 6,836,530 | B2 | 12/2004 | Singer et al. | |
| 6,870,896 | B2 | 3/2005 | Protopopov | |
| 6,927,748 | B2 | 8/2005 | Hughes et al. | |
| 6,947,521 | B2 | 9/2005 | Wernick et al. | |
| 6,947,522 | B2 * | 9/2005 | Wilson et al. | 378/125 |
| 6,953,643 | B2 | 10/2005 | Bordillon | |
| 6,980,378 | B2 | 12/2005 | Lee | |
| 6,987,616 | B2 | 1/2006 | Tamada et al. | |
| 6,991,895 | B1 | 1/2006 | Yen et al. | |
| 7,012,989 | B2 | 3/2006 | Holland et al. | |
| 7,062,015 | B2 | 6/2006 | Lewis | |
| 7,076,025 | B2 | 7/2006 | Hasnah et al. | |
| 7,082,182 | B2 * | 7/2006 | Zhou et al. | 378/10 |
| 7,095,510 | B2 | 8/2006 | Fukui | |
| 7,120,228 | B2 | 10/2006 | Yokhin et al. | |
| 7,183,547 | B2 | 2/2007 | Yun et al. | |
| 7,193,767 | B1 | 3/2007 | Peeri | |
| 7,224,528 | B2 | 5/2007 | Phillips et al. | |
| 7,242,744 | B2 | 7/2007 | Brauss | |
| 7,245,696 | B2 | 7/2007 | Yun et al. | |
| 7,330,530 | B2 | 2/2008 | Chapman | |
| 7,352,845 | B2 | 4/2008 | Uda | |
| 7,409,041 | B2 | 8/2008 | Grassmann et al. | |
| 7,421,060 | B2 | 9/2008 | Zienert et al. | |
| 7,431,464 | B2 | 10/2008 | Park | |
| 7,443,952 | B2 | 10/2008 | Dosho et al. | |
| 7,469,037 | B2 * | 12/2008 | Wernick et al. | 378/82 |
| 7,471,766 | B2 | 12/2008 | Dosho | |
| 7,535,992 | B2 | 5/2009 | Taguchi et al. | |
| 7,542,547 | B2 | 6/2009 | Kogan | |
| 7,564,947 | B2 | 7/2009 | Cernik | |
| 7,639,774 | B2 * | 12/2009 | De Man et al. | 378/9 |
| 7,646,849 | B2 | 1/2010 | Iwasaki et al. | |
| 7,711,088 | B2 | 5/2010 | Gibson et al. | |
| 7,724,871 | B2 | 5/2010 | Boyden et al. | |
| 7,742,563 | B2 | 6/2010 | Edic et al. | |
| 7,742,564 | B2 | 6/2010 | Parham et al. | |
| 7,809,114 | B2 * | 10/2010 | Zou et al. | 378/134 |
| 7,817,779 | B2 * | 10/2010 | Ando | 378/71 |
| 7,991,114 | B2 * | 8/2011 | Okunuki et al. | 378/62 |
| 2003/0112421 | A1 | 6/2003 | Smith | |
| 2003/0149357 | A1 | 8/2003 | Liu | |
| 2004/0101676 | A1 | 5/2004 | Phillips et al. | |
| 2004/0121241 | A1 | 6/2004 | Kodama | |
| 2004/0196957 | A1 | 10/2004 | Ando | |
| 2005/0062928 | A1 | 3/2005 | Yau et al. | |
| 2005/0069696 | A1 | 3/2005 | King et al. | |
| 2005/0269818 | A1 | 12/2005 | Forde | |
| 2006/0039532 | A1 | 2/2006 | Wu et al. | |
| 2007/0013983 | A1 | 1/2007 | Kitamura et al. | |
| 2007/0024828 | A1 | 2/2007 | Liao et al. | |
| 2007/0291896 | A1 | 12/2007 | Parham et al. | |

FOREIGN PATENT DOCUMENTS

| | | |
|---|---|---|
| WO | WO 2007/087328 A2 | 8/2008 |
| WO | 2010065532 A2 | 6/2010 |
| WO | WO 2010/065532 A2 | 6/2010 |
| WO | WO 2010/141734 A2 | 12/2010 |
| WO | WO 2010/141735 A2 | 12/2010 |
| WO | PCT/US2010037276 | 12/2011 |

OTHER PUBLICATIONS

Notification of Transmittal of International Preliminary Examination Report for PCT International Application No. PCT/US07/01836 to the University of North Carolina at Chapel Hill.

Written Opinion of the International Searching Authority for PCT International Application No. PCT/US07/01836 to the University of North Carolina at Chapel Hill.
Patent Application No. 2007/80009742.9 has been published in the Chinese Patent Gazette on Apr. 8, 2009 as Publication No. CN 101405596 A.

Indian Patent Application No. 4155/CHENP/2008 has been published in the Patent Office Journal on Mar. 13, 2009.
Related U.S. Appl. No. 12/793,228 to Dean Connor.

* cited by examiner

SYSTEMS AND METHODS FOR DETECTING AN IMAGE OF AN OBJECT BY USE OF X-RAY BEAMS GENERATED BY MULTIPLE SMALL AREA SOURCES AND BY USE OF FACING SIDES OF ADJACENT MONOCHROMATOR CRYSTALS

CROSS REFERENCE TO RELATED APPLICATIONS

This application claims the benefit of U.S. provisional patent application No. 61/183,988, filed Jun. 4, 2009, and U.S. provisional patent application No. 61/183,989, filed Jun. 4, 2009, the contents of which are incorporated herein in their entireties.

TECHNICAL FIELD

The subject matter disclosed herein relates to X-ray imaging. More particularly, the subject matter disclosed herein relates to systems and methods for detecting an image of an object by use of X-ray beams generated by a plurality of small area sources, and by use of facing sides of adjacent monochromator crystals.

BACKGROUND

X-ray imaging has been used in a variety of fields for imaging objects. For example, X-ray imaging has been used extensively in the medical field for non-destructive testing and X-ray computed tomography (CT). Various other types of technology are also being used for medical imaging. For example, diffraction enhanced imaging (DEI) is an X-ray imaging technique that dramatically extends the capability of conventional X-ray imaging.

The DEI technique is an X-ray imaging modality capable of generating contrast from X-ray absorption, X-ray refraction, and ultra-small angle scatter rejection (extinction). In contrast, conventional X-ray imaging techniques measure only X-ray attenuation. The DEI absorption image and peak image show similar information to a conventional radiograph, except that it is virtually free of scatter degradation. DEI utilizes perfect crystal diffraction from to convert small angular changes in a transmitted x-ray beam into large intensity changes in an image. Thus, DEI is well suited to soft-tissue imaging, and very promising for mammography.

The use of a silicon analyzer crystal in the path of the X-ray beam generates two additional forms of image contrast, X-ray refraction, and extinction (ultra small angle scatter rejection). DEI utilizes highly collimated X-rays prepared by X-ray diffraction from perfect single-crystal silicon. These collimated X-rays are of single X-ray energy, practically monochromatic, and are used as the beam to image an object.

Objects that have very little absorption contrast may have considerable refraction and extinction contrast, thus improving visualization and extending the utility of X-ray imaging. Applications of DEI techniques to biology and materials science have generated significant gains in both contrast and resolution, indicating the potential for use in mainstream medical imaging. An area of medicine where DEI may be particularly effective is in breast imaging for cancer diagnosis, where the diagnostic structures of interest often have low absorption contrast, making them difficult to see. Structures with low absorption contrast, such as the spiculations extending from a malignant mass, have high refraction and ultra-small angle scatter contrast. It is desirable to provide a DEI system with the capability to increase both the sensitivity and specificity of X-ray-based breast imaging.

Multiple studies have demonstrated improved image contrast in both medical and industrial applications of DEI. Advantages of DEI systems over conventional X-ray imaging systems in the medical field include a dramatic reduction in patient radiation dose and improved image quality. The dose reduction is due to the ability of DEI systems to function at higher X-ray energies. X-ray absorption is governed by the photoelectric effect, $Z^2/E^3$, where Z is the atomic number and E is the photon energy.

A monoenergetic radiograph contains several components that can affect image contrast and resolution: a coherently scattered component $I_c$, an incoherently scattered component $I_I$, and a transmitted component. X-rays passing through an object or medium where there are variations in density can be refracted, resulting in an angular deviation. Specifically, deviations in the X-ray range result from variations in ρt along the path of the beam, where ρ is the density and t is the thickness. A fraction of the incident photons may also be diffracted by structures within an object, which are generally on the order of milliradians and referred to as small angle scattering. The sum total of these interactions contributed to the recorded intensity in a radiograph $I_N$, which can be represented by the following equation:

$$I_N = I_R + I_D + I_C + I_I$$

System spatial resolution and contrast will be degraded by the contributions of both coherent and incoherent scatter. Anti-scatter grids are often used in medical imaging to reduce the contribution of scatter, but their performance is limited and use of a grid often requires a higher dose to compensate for the loss in intensity.

The DEI technique utilizes a silicon analyzer crystal in the path of the post-object X-ray beam to virtually eliminate the effects of both coherent and incoherent scatter. The narrow angular acceptance window of the silicon analyzer crystal is referred to as its rocking curve, and is on the order of microradians for the X-ray energies used in DEI. The analyzer acts as an exquisitely sensitive angular filter, which can be used to measure both refraction and extinction contrast. Extinction contrast is defined as the loss of intensity from the incident beam due to scattering, which can produce substantial improvements in both contrast and resolution.

The Darwin Width (DW) is used to describe reflectivity curves, and is approximately the Full Width at Half Maximum (FWHM) of the reflectivity curve. Points at −½ DW and +½ DW are points on the curve with a steep slope, producing the greatest change in photon intensity per microradian for a particular analyzer reflection and beam energy. Contrast at the peak of the analyzer crystal rocking curve is dominated by X-ray absorption and extinction, resulting in near scatter-free radiographs. Refraction contrast is highest where the slope of the rocking curve is greatest, at the −½ and +½ DW positions. One DEI based image processing technique uses these points to extract the contrast components of refraction and apparent absorption from these image pairs.

The following paragraph describes of this technique for extracting the contrast components of refraction and apparent absorption from an image pair. When the analyzer crystal is set to an angle representing +/−½ DW for a given reflection and beam energy, the slope of the rocking curve is relatively consistent and can be represented as a two-term Taylor series approximation as represented by the following equation:

$$R(\theta_0 + \Delta\theta_z) = R(\theta_0) + \frac{dR}{d\theta}(\theta_0)\Delta\theta_z.$$

If the analyzer crystal is set to the low-angle side of the rocking curve (−½ DW), the resulting image intensity can be represented by the following equation:

$$I_L = I_R\left(R(\theta_L) + \frac{dR}{d\theta}\bigg|_{\theta=\theta_L} \Delta\theta_z\right).$$

The recorded intensity for images acquired with the analyzer crystal set to the high-angle position (+½ DW) can be represented by the following equation:

$$I_H = I_R\left(R(\theta_H) + \frac{dR}{d\theta}(\theta_H)\Delta\theta_z\right).$$

These equations can be solved for the changes in intensity due to apparent absorption ($I_R$) and the refraction in angle observed in the z direction ($\Delta\theta_Z$) represented by the following equation:

$$\Delta\theta_Z = \frac{I_H R(\theta_L) - I_L R(\theta_H)}{I_L\left(\frac{dR}{d\theta}\right)(\theta_H) - I_H\left(\frac{dR}{d\theta}\right)(\theta_L)}$$

$$I_R = \frac{I_L\left(\frac{dR}{d\theta}\right)(\theta_H) - I_H\left(\frac{dR}{d\theta}\right)(\theta_L)}{R(\theta_L)\left(\frac{dR}{d\theta}\right)(\theta_H) - R(\theta_H)\left(\frac{dR}{d\theta}\right)(\theta_L)}.$$

These equations can be applied to the high and low angle images on a pixel-by-pixel basis to separate the two contrast elements into what is known as a DEI apparent absorption and refraction image. However, it is important to note that each of the single point rocking curve images used to generate DEI apparent absorption and refraction images is useful.

Development of a clinical DEI imager may have significance for women's health and medical imaging in general for the following reasons: (1) DEI has been shown to produce very high contrast for the features that are most important to detection and characterization of breast cancer; (2) the physics of DEI allows for imaging at higher x-ray energies than used with absorption alone; and (3) the ability of DEI to generate contrast without the need of photons to be absorbed dramatically reduces ionization, and thus reduces the absorbed dose.

Further, screen-film mammography has been studied extensively for the last 40 years, and because of many large randomized screening trials, it is known to reduce breast cancer mortality by approximately 18-30%. The rate of breast cancer death in the last few years has begun to decline, likely due in part to the widespread use of this imaging test. However, standard screen-film mammography is neither perfectly sensitive nor highly specific. Dense breast tissue and diffuse involvement of the breast with tumor tends to reduce the sensitivity of screening mammography. For women with dense breasts, lesions that develop are difficult to see because their ability to absorb photons is not much greater than the surrounding adipose tissue, generating little contrast for visualization. Approximately 10-20% of breast cancers that are detected by self-examination or physical examination are not visible by screen-film mammography. In addition, when lesions are detected by mammography and biopsy, only 5-40% of lesions prove to be malignant. Furthermore, approximately 30% of breast cancers are visible in retrospect on prior mammograms.

Current DEI and DEI imaging processing techniques are based heavily on conventional imaging theory and rely, at least in part, on X-ray absorption for image generation. Thus, objects imaged using these techniques absorb radiation. Such radiation exposure is undesirable in applications for medical imaging given concerns of dose, and this reasoning places considerable engineering limitations that make clinical and industrial translation challenging. Thus, it is desirable to provide DEI and DEI techniques that produce high quality images and that rely less on absorption but produce images with equivalent diagnostic quality and feature visualization. In addition, it is desirable to reduce DEI imaging time, which can be affected by the significant reduction of beam flux in DEI monochromators.

SUMMARY

Systems and methods for detecting an image of an object by use of X-ray beams generated by multiple small area sources are disclosed herein. According to an aspect of the disclosed subject matter, a system can include small area sources having dimensions between 0.2 and 2 mm in the vertical, horizontal directions, and/or any other direction. In an example embodiment, a method may include providing a plurality of small area sources. A plurality of first X-ray beams may be generated by using the small area sources. A plurality of monochromator crystals may be positioned to intercept the plurality of first X-ray beams such that a plurality of second X-ray beams each having predetermined energy levels is produced. Further, an object to be imaged may be positioned in paths of the second x-ray beams for transmission of the second X-ray beams through the object and emitting from the object a plurality of transmission X-ray beams. The X-ray beams may be directed at angles of incidence upon a plurality of analyzer crystals. Further, an image of the object may be detected based upon beams diffracted from the analyzer crystals.

According to another aspect of the disclosed subject matter, a system can comprise an X-ray generation device configured to generate a plurality of first X-ray beams. The system can include monochromator crystals including first and second sides. The first sides of the monochromator crystals are positioned in predetermined positions to directly intercept the plurality of first X-ray beams for generating a plurality of second X-ray beams. The second sides of the monochromator crystals are positioned to intercept the plurality of second X-ray beams such that a plurality of third X-ray beams is produced for transmission through an object. A plurality of analyzer crystals are positioned to intercept transmitted X-ray beams at angles of incidence of the analyzer crystals. An image detector is configured to detect an image of the object from beams diffracted from the analyzer crystals.

Further, systems and methods for detecting an image of an object by use of X-ray beams generated by utilizing facing sides of adjacent monochromator crystals are also disclosed. According to an aspect, a system using facing sides of adjacent monochromator crystals can include an X-ray generation device configured to generate a plurality of first X-ray beams. The system can include monochromator crystals including first and second sides. The first sides of the monochromator crystals are positioned in predetermined positions to directly intercept the plurality of first X-ray beams for generating a plurality of second X-ray beams. The second sides of the monochromator crystals are positioned to intercept the plurality of second X-ray beams such that a plurality of third X-ray beams is produced for transmission through an object. A plurality of analyzer crystals are positioned to intercept transmitted X-ray beams at angles of incidence of the analyzer crystals. An image detector is configured to detect an image of the object from beams diffracted from the analyzer crystals.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the disclosed subject matter is not limited to the specific methods and instrumentalities disclosed. In the drawings.

DETAILED DESCRIPTION

Figure 1:
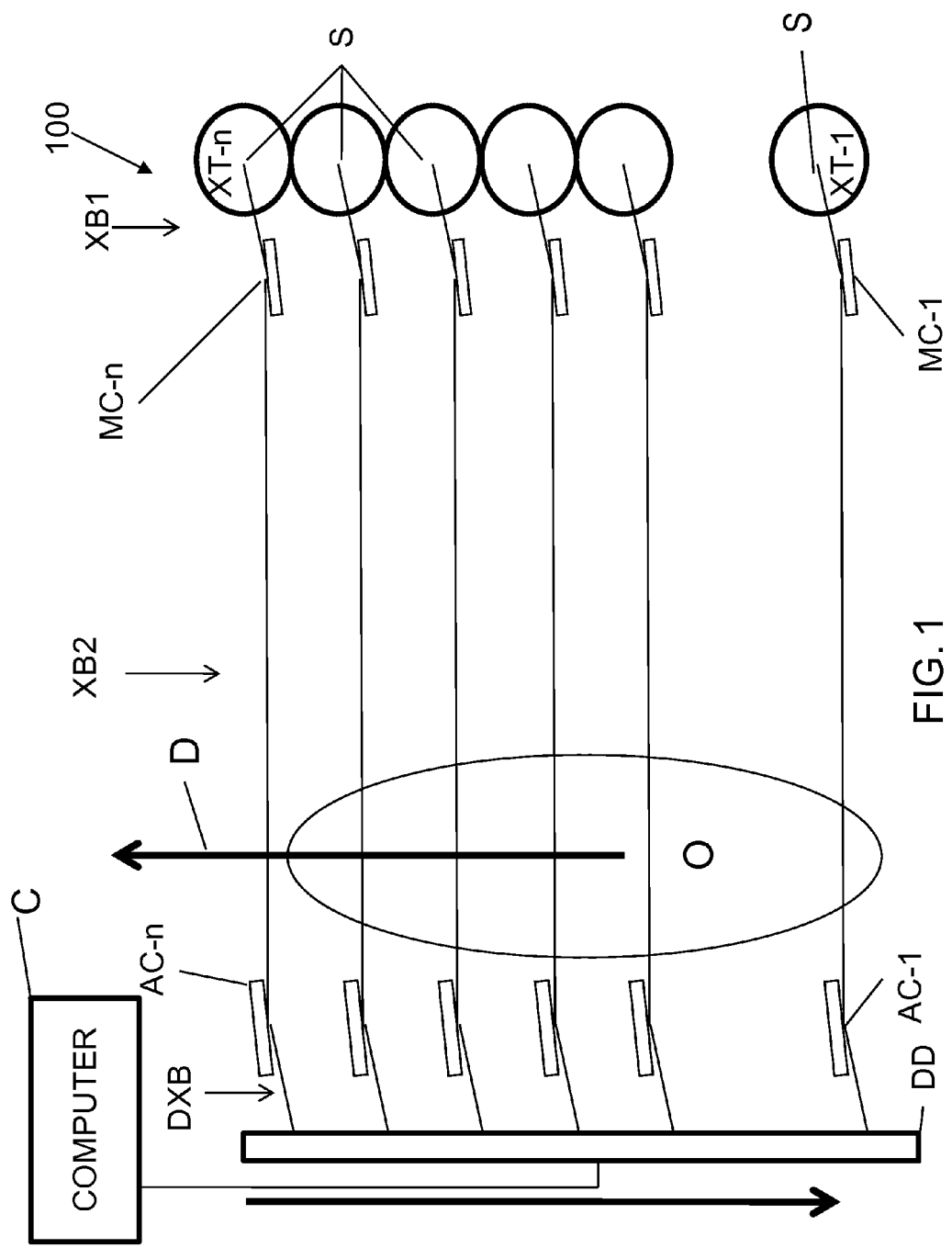
FIGS. 1-11 are schematic diagrams of different example DEI systems including multiple monochromator crystals and multiple small area sources according to embodiments of the subject matter described herein.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

The subject matter described herein discloses improved DEI and DEI systems and related methods for detecting an image of an object. In particular, the subject matter described herein includes systems and methods for detecting an image of an object using X-rays generated by multiple small area sources. According to one aspect, the subject matter described herein can include a method for detecting an image of an object by providing a plurality of small area sources. A plurality of first X-ray beams can be generated by using the small area sources. A plurality of monochromator crystals can be positioned to intercept the plurality of first X-ray beams such that a plurality of second X-ray beams each having predetermined energy levels is produced. Further, an object to be imaged can be positioned in paths of the second x-ray beams for transmission of the second X-ray beams through the object and emitting from the object a plurality of transmission X-ray beams. The X-ray beams may be directed at angles of incidence upon a plurality of analyzer crystals. Further, an image of the object can be detected based upon beams diffracted from the analyzer crystals. These systems and methods can be advantageous, for example, because they can provide extremely low dose in medical applications, fast scan times, high resolution, and relatively low operation and build costs. Further, for example, these systems can be constructed into a compact unit and be readily usable in clinical and industrial applications. Additional description about these systems and related methods are described in further detail herein.

According to another aspect, the subject matter described herein can include a system comprising an X-ray generation device configured to generate a plurality of first X-ray beams. The system can include monochromator crystals including first and second sides. The first sides of the monochromator crystals are positioned in predetermined positions to directly intercept the plurality of first X-ray beams for generating a plurality of second X-ray beams. The second sides of the monochromator crystals are positioned to intercept the plurality of second X-ray beams such that a plurality of third X-ray beams is produced for transmission through an object. A plurality of analyzer crystals are positioned to intercept transmitted X-ray beams at angles of incidence of the analyzer crystals. An image detector is configured to detect an image of the object from beams diffracted from the analyzer crystals. An image of the object may be detected based upon beams diffracted from the analyzer crystals. These systems and methods can be advantageous, for example, because they can provide extremely low dose in medical applications, fast scan times, high resolution, and relatively low operation and build costs. Further, for example, these systems can be constructed into a compact unit and be readily usable in clinical and industrial applications. Additional description about these systems and related methods are described in further detail herein.

An image processing technique using DEI in accordance with the subject matter described herein can use images acquired at symmetric points of the rocking curve to generate apparent absorption and refraction images of an object. A DEI apparent absorption image is similar to a conventional radiograph image, but exhibits much greater contrast owing to scatter rejection. DEI refraction images can depict the magnitude of small beam deflections caused by large-scale refractive-index features (features of a size at or greater than the system resolution). A DEI extinction image is generated at points on the rocking curve where the primary mechanism of contrast is due to photons that have been scattered by an object on the order of microradians. Another DEI based imaging processing technique is referred to as Multiple Image Radiography (MIR) which uses multiple points on the rocking curve to generate quantitative images representing an object's X-ray absorption, refraction, and ultra-small angle scatter. Systems and methods can generate images at any point on the analyzer rocking curve, and can thus be used to generate: (1) single image DEI at any analyzer position; (2) DEI apparent absorption and refraction images; and (3) mass density images. The ability to generate the raw image data required for these processes and any other DEI based processing technique are useful for all DEI based processing techniques. In addition, systems and methods described herein are amenable for use in computed tomography, and can provide the raw data for use in any DEI-based computed tomography algorithm.

As understood, a small area source may refer to any source capable of generating X-ray beams from a small area in space. For example, an X-ray tube may include multiple small area sources for emitting X-ray beams from multiple points. The small area sources may be within the same X-ray tube source. Alternatively or in addition to being a part of a system as disclosed herein, multiple X-ray tube sources may each provide one or more small area sources and be used together for generating multiple X-ray beams.

The subject matter disclosed herein provides an additional advantage of providing spacing between individual DEI crystal optics arrays and improved heat dissipation with the source anode due the power load being delivered to several, separated points, both advancements over a single-source, multiple-beam design. This applies to one beam per small area source (wherein the number of beams equals the number of small area sources) as well as multiple beams per source point (if each source generates n beams, then the beams will number n times the number of small area sources).

The subject matter disclosed herein is advantageous over previous DEI systems and methods, because it allows for greater mechanical separation between the individual optical elements, thereby solving the problem of potential mechanical interference between monochromator crystals. By using multiple small area sources as described herein, rather than having a single, very high power source location, the power load can be divided amongst several source locations, thus the heat load to the anode may be distributed over a larger area, which can allow for longer operating times for the tube sources. By spacing out the small area sources, the monochromator crystal sizes, as well as the size of the electromechanical control systems, can be larger as compared to previous systems. In addition, the subject matter disclosed herein can allow for greater distribution of the heating load to the anode for decreasing time between imaging sessions.

Approaches to DEI or analyzer-based imaging as described herein can use large X-ray beams at a sample or object location to image the object without the need to scan the X-ray beam. These large area X-ray beams can be generated through the use of asymmetric crystals, an X-ray line source, or a combination of the two. As with the techniques and systems presented herein, the other techniques may require a high-power X-ray tube source operating at a peak voltage well above the K$\alpha$1 emission energy of their respective source in order to generate sufficient K$\alpha$1 flux for a small imaging time. The high energy X-rays generated by the high peak voltage will be readily scattered by the monochromator crystals, and this scattered radiation dose delivered to the object to be imaged. Stated in another way, there will be a "line-of-sight" between the scatter locations on the monochromator crystals and the object to be imaged over which there cannot be significant radiation shielding to stop the scattered radiation from reaching the object to be imaged. This contribution of scattered radiation to the radiation dose delivered to the object to be imaged can be overcome through the use of a multiple small-vertical height X-ray beam system, which can be created through the use of an array of small area X-ray beams. Any radiation that does not propagate along the narrow beam path can be filtered out by high-Z shielding, and therefore only a minimal amount of scattered radiation will reach the object to be imaged.

A DEI system according to one embodiment of the subject matter described herein can include multiple monochromator crystals for rejecting particular X-rays emitted by multiple X-ray small area sources. FIGS. 1-11 are schematic diagrams of different example DEI systems including multiple monochromator crystals and multiple small area sources according to embodiments of the subject matter described herein. The DEI systems are operable to produce images of an object by use of the X-ray beams generated by the multiple small area sources. The DEI systems can include multiple small area sources operable to produce a polychromatic X-ray beam, generally designated XB1. X-ray beams XB1 can include photons having different energies. In one example, the X-ray beams are generated by one or more tungsten X-ray tubes each having a small area source from which an X-ray beam. In another example, a system may include multiple X-ray tube sources that each provide one or more small area sources and may be used together for generating multiple X-ray beams.

Referring again to FIG. 1, a DEI system, generally designated 100, includes a number N X-ray tubes XT-1-XT-N, each including at least one small area source S, for generating multiple X-ray beams XB1. An array of collimators (not shown) may be positioned adjacent each small area source S for blocking a portion of each of X-ray beams XB1 that fall outside an angular acceptance window of respective monochromator crystals MC-1-MC-n. System 100 can also include other collimators positioned between small area sources XT-1-XT-N and monochromator crystals MC-1-MC-n for blocking a portion of X-ray beams XB1 that falls outside an angular acceptance window of the monochromator crystals MC-1-MC-n. The collimators can define a slit or hole through which a portion of X-ray beams XB1 can pass to monochromator crystals MC-1-MC-n. Further, the collimators can be made of any suitable material for blocking X-ray beams such as lead.

The monochromator crystals MC-1-MC-n can be configured to select a predetermined energy of a portion of X-ray beams XB1 incident thereon. In one example, a monochromator crystal is a silicon [333] monochromator crystal adapted to reject the majority of photons of its respective X-ray beams that do not have a desired energy. For the case of a tungsten X-ray tube, there can be a range of beam energies that are reflected by the silicon monochromator crystal. In this case, the characteristic emission lines of the X-ray beams are 59.13 keV (K$\alpha$1) and 57.983 (K$\alpha$2), and the Bremsstrahlung radiation that falls within the narrow angular acceptance window of the monochromator crystal. The brightness of the bremsstrahlung radiation is several orders of magnitude less than the two K$\alpha$ emission lines.

An X-ray beam may be scattered by its respective monochromator crystal in several different directions. Another array of collimators (not shown) may be positioned between the monochromator crystals MC-1-MC-n and the object O for blocking a portion of the X-ray beam that falls outside an angular acceptance window of its corresponding analyzer crystal, one of analyzer crystals AC-1-AC-n. Each collimator can define a slit or hole through which a portion of one of the X-ray beams can pass towards its analyzer crystal for interception by the analyzer crystal.

The analyzer crystals AC-1-AC-n can be rotated for measuring the amount of radiation traveling in a particular direction. The angular reflectivity function of the crystal system is called the intrinsic rocking curve, and this property is used to generate image refraction contrast. If an X-ray photon is deviated towards the peak of the rocking curve, its reflectivity, and thus intensity will increase. If an object feature causes a photon to be deflected down the rocking curve, or away from the peak reflectivity position, it will cause a reduction in intensity.

A sample or object O can be imaged in air or immersed in a coupling medium, such as water. The use of a coupling medium can be used to reduce the index gradient between the air and the object O to be imaged, thus allowing the incident X-rays to pass into the object without experiencing significant refraction at the air-object interface. This is not necessary for most objects, but it is an application of the DEI method and can be used to improve the internal contrast of an object.

In one example, a monochromator crystal is a symmetric crystal which is narrow in one dimension. A symmetric crystal's lattice planes (the atomic layers that contribute to diffracting the X-ray beam) are parallel to the surface of the crystal. A symmetric crystal preserves the vertical height of the corresponding X-ray source in the incoming beam. In comparison, an asymmetric crystal modifies the divergence and size of the incoming beam. In this example of a monochromator crystal being a symmetric crystal, two-dimensional imaging of large imaging fields (e.g., imaging fields of about 25 cm by 20 cm) can be achieved by scanning a sample object and a detector using a symmetric crystal. One exemplary advantage of a symmetric crystal over an asymmetric crystal is that the asymmetric crystal requires a large monochromator crystal to prepare the imaging beam (e.g., selecting and collimating X-rays), imposing a severe limitation on the perfection of the large crystal. Further, the size of an asymmetric crystal increases with increasing X-ray beam energy, thus making it impractical for X-rays of about 59.13 keV. In contrast, for example, a symmetric monochromator crystal used in accordance with the subject matter described herein can utilize 59.13 keV X-rays with a modest sized crystal of about 30 mm in length. An advantage, over single-beam DEI, of the system and methods proposed disclosed herein, with multiple sources, is that this scan range can be greatly reduced, because of much better spatial coverage of the beams (i.e. if you have a required 25 cm scan range, and 10 beams, then the object will only have to be scanned through a range of 2.5 cm).

Referring again to FIG. 1, the object O can be positioned in the path of X-ray beams XB2 (the X-ray beams resulting for the interaction of X-ray beams XB1 with the monochromator crystals MC-1-MC-n) by, for example, a scanning stage (not shown) for imaging of the object O. The object O can be scanned in a direction D, which is approximately perpendicular to the direction of X-ray beams XB2. During scanning of the object O, X-ray beams XB2 can pass through object O and can be analyzed by analyzer crystals AC-1-AC-n, which can be silicon [333] crystals that match monochromator crystals MC-1-MC-n. X-ray beams XB2 incident on analyzer crystals AC-1-AC-n can each diffract (resulting in diffraction X-ray beams, generally designated DXB) for interception by a digital detector (or image plate) DD. Digital detector DD can detect the diffracted X-ray beams DXB and generate electrical signals representative of the intercepted X-ray beams DXB.

The electrical signals can be communicated to a computer C for image analysis and display to an operator. The computer C can be configured to generate an absorption image, an image showing refraction effects, and an image depicting ultra-small-angle scattering, the types of which are described in more detail below.

The monochromator crystals can propagate their respective x-ray beams as a horizontally-divergent (FIG. 4) and partially vertically divergent (see FIG. 3) fan beam. The fan beam can be collimated with one or more collimators to shield against undesired X-rays, resulting in clear DEI images and low subject dose. In contrast to a two-dimensional beam, a fan beam can be more readily controlled for the shielding of undesired X-rays.

Figure 2:
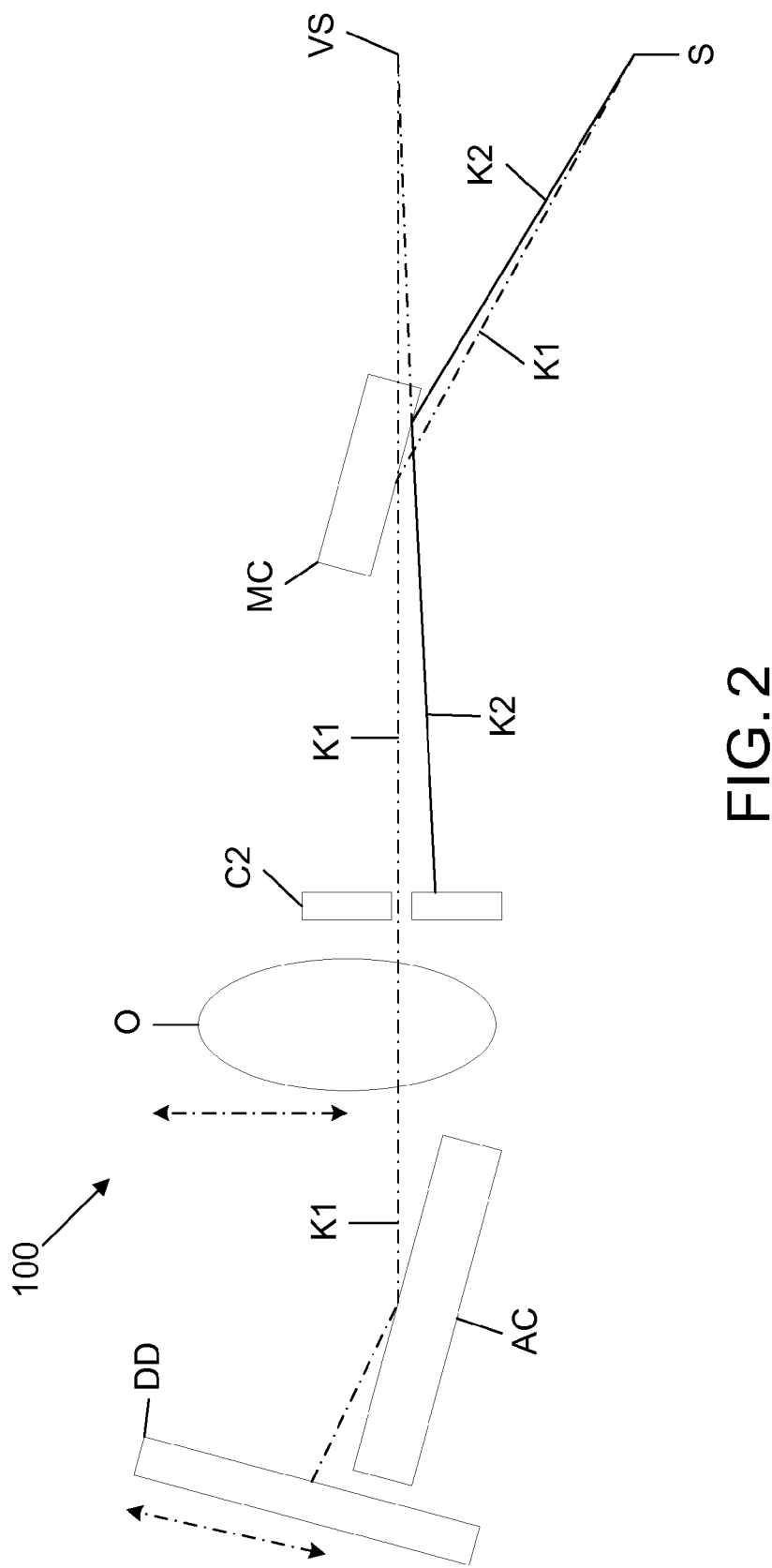
Figure 3:
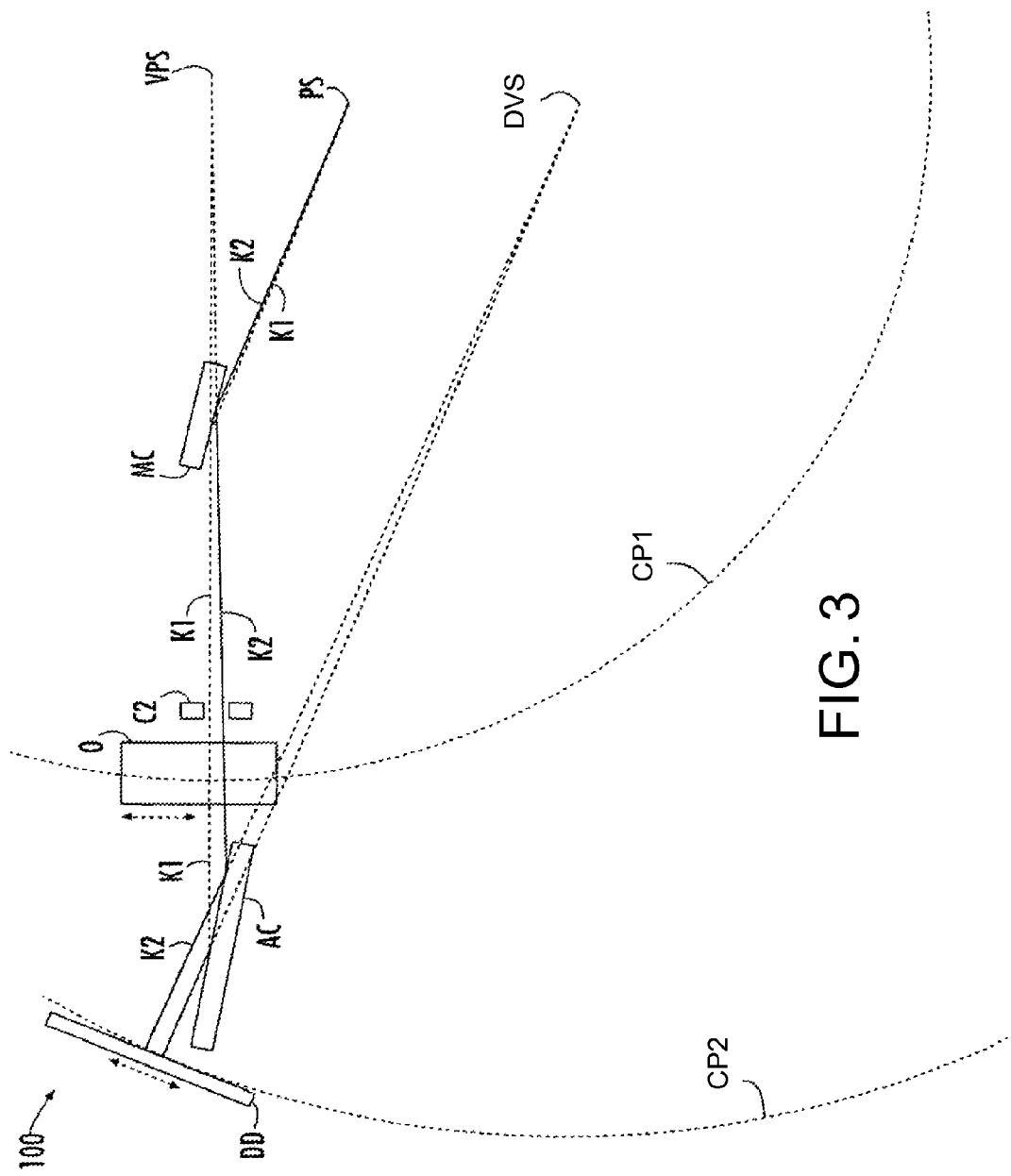

Referring now to FIGS. 2 and 3, the DEI system 100 is shown in different operation modes. For clarity, the X-ray beam generated by only one small area source S is shown. Characteristic emission lines $K\alpha 1$ K1 and $K\alpha 2$ K2 of the X-ray beam are generated by small area source S. Emission lines $K\alpha 1$ K1 and $K\alpha 2$ K2 originate from the same small area source S. As stated above, monochromator crystal MC rejects the majority of photons of the X-ray beam that do not have the desired energy. In this case, emission lines $K\alpha 1$ K1 and $K\alpha 2$ K2 and bremsstrahlung radiation pass monochromator crystal MC and are redirected towards an analyzer crystal AC as shown.

Collimator C2 is positioned in a path of emission lines $K\alpha 1$ K1 and $K\alpha 2$ K2. Collimator C2 defines an adjustable slit through which emission lines can be selectively passed towards analyzer crystal AC. In the first operational mode shown in FIG. 2, the slit is adjusted for an aperture of the vertical size of the X-ray source at a distance of about 400 mm from the small area source S, and positioned such that emission line $K\alpha 1$ K1 passes collimator C2 and $K\alpha 2$ K2 is blocked. Thus, collimator C2 removes all X-rays except for the X-rays from emission line $K\alpha 1$ K1 and a very narrow range of bremsstrahlung radiation. In this mode, the beam is not vertically divergent and thus the object O and detector DD are scanned at the same scanning speed, in opposite directions. This mode yields a maximum possible out-of-plane resolution (the direction of DEI's contrast), but at the cost of removing a portion of the X-rays from the X-ray beam, thereby necessitating increased exposure time. The virtual small area source for the object O is designated VS.

Referring now to FIG. 3, in the second operational mode, emission lines $K\alpha 1$ K1 and $K\alpha 2$ K2 and the bremsstrahlung radiation at nearby energies are passed through the collimator C2. The slit of collimator C2 is adjusted for an aperture of about 2.0 mm at a distance of about 400 mm from the small area source S and positioned such that emission lines $K\alpha 1$ K1 and $K\alpha 2$ K2 and the bremsstrahlung radiation passes collimator C2. In this mode, the beam divergence is taken into account. In order to avoid image blurring, the object O and detector DD can be scanned at the same angular speed. The relative scanning speeds of detector DD and the sample stage on which the object O is placed can be determined by the source-to-object distance and the source-to-detector distance (where the distances are taken along the beam path). The beam divergence in this mode can lead to lower resolution out-of-plane, but this mode has the advantage of passing more X-rays and thus allows for a faster exposure time. The virtual small area source for detector DD is designated DVS. Circle portions CP1 and CP2 are centered at the virtual source points for the object O and detector DD, respectively.

Further, in one embodiment of using the second mode, the Bremsstrahlung radiation at x-ray energies that are different from the K alpha lines can be captured. Thus, in this embodiment, the system is tunable in x-ray energy and is not limited to the characteristic emission energies. This functionality can be achieved by changing the incident angle of the monochromator crystal and the analyzer crystal. In one example, this functionality can be achieved by changing the incident angle to 11.4 degrees, following the Bragg's law, and replacing the Copper filter with an Aluminum filter. In this example, imaging can occur at 30 keV x-ray energy. X-ray energies lower than the Tungsten emission line energies can be utilized for relatively thin objects.

In one example, the copper filter can be configured to remove about 19 keV bremsstrahlung radiation for reducing or eliminating unwanted crystal reflections and harmonics. Images have the potential to be degraded without this filtering.

Figure 4:
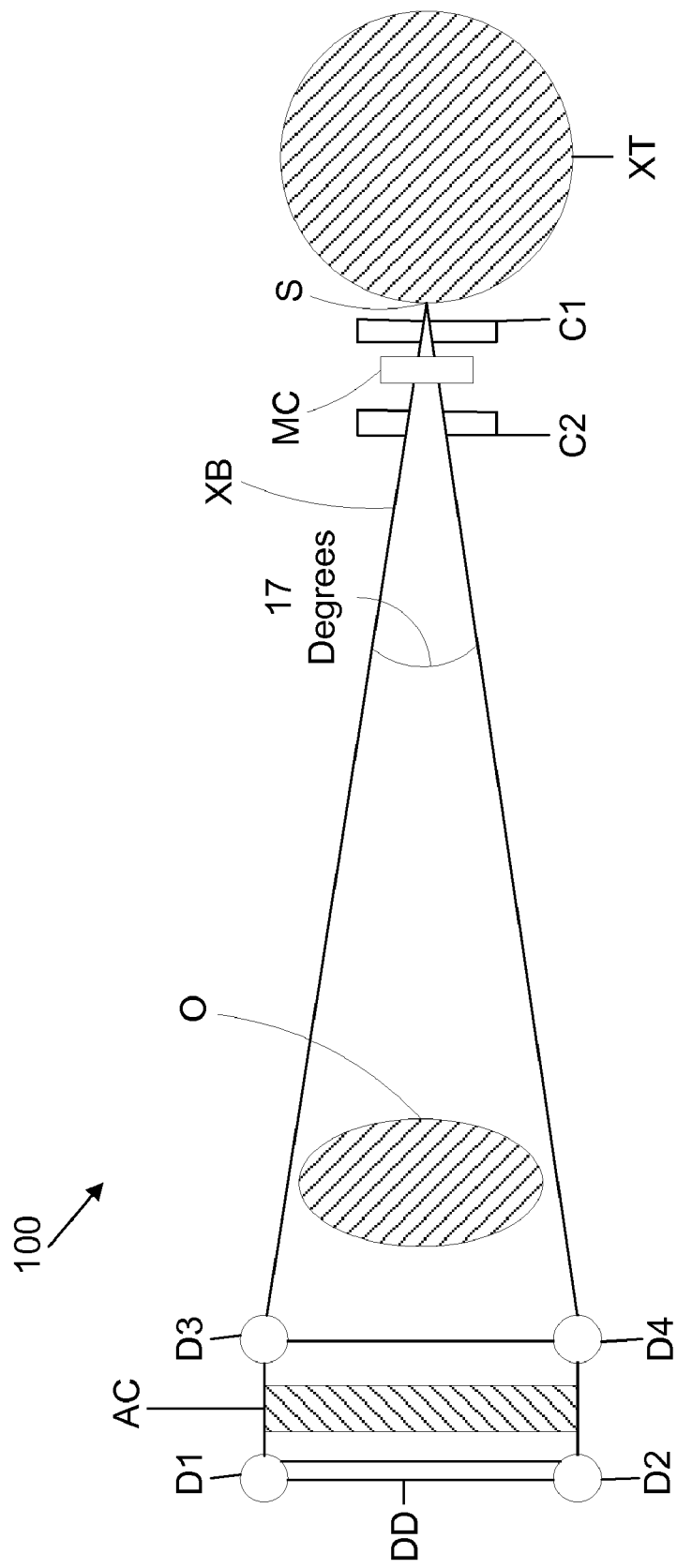

FIG. 4 is a top schematic view illustrating the DEI system 100 of FIG. 1 according to an embodiment of the subject matter described herein. For clarity, the X-ray beam XB generated by only one small area source of an X-ray tube is shown. Referring to FIG. 4, X-ray beam XB are generated by a source of X-ray tube XT. Collimators C1 and C2 block the horizontal spread of the portion of X-ray beam XB to define the angular spread of the X-ray beam XB and its horizontal size at the object O position. The portion of X-ray beam XB that passes through collimators C1 and C2 is the X-ray beam portion that passes through slits in the collimators.

The DEI system 100 can include right and left post-analyzer crystal sodium iodide detectors D1 and D2, respectively, and right and left post-monochromator crystal sodium iodide detectors D3 and D4, respectively. Detectors D3 and D4 are used to ensure alignment of the monochromator crystals (MC) and detectors D1 and D2 are used to ensure analyzer crystal (AC) alignment. These detectors are used to measure the intensity of the diffracted X-ray beam being emitted from the monochromator crystal MC, or the analyzer crystal AC. For system alignment, detectors D1 and D2 are placed in the post analyzer crystal AC X-ray beam XB. If the analyzer crystal is not tuned to the desired angle, the intensity measured by the detectors D1 and D2 will show this and the system can be adjusted. The same is true for the detectors D3 and D4 in the post-monochromator crystal MC X-ray beam XB. In addition, detectors D1-D4 can be used to measure X-ray beam XB in real time and adjust the analyzer crystal, D1 and D2, chi (angle as measured about the axis along the X-ray beam path) or monochromator crystal chi, D3 and D4. The use of these detectors to set, measure, and adjust the analyzer crystal AC and monochromator crystal MC can be important for successful DEI image acquisition.

Figure 5:
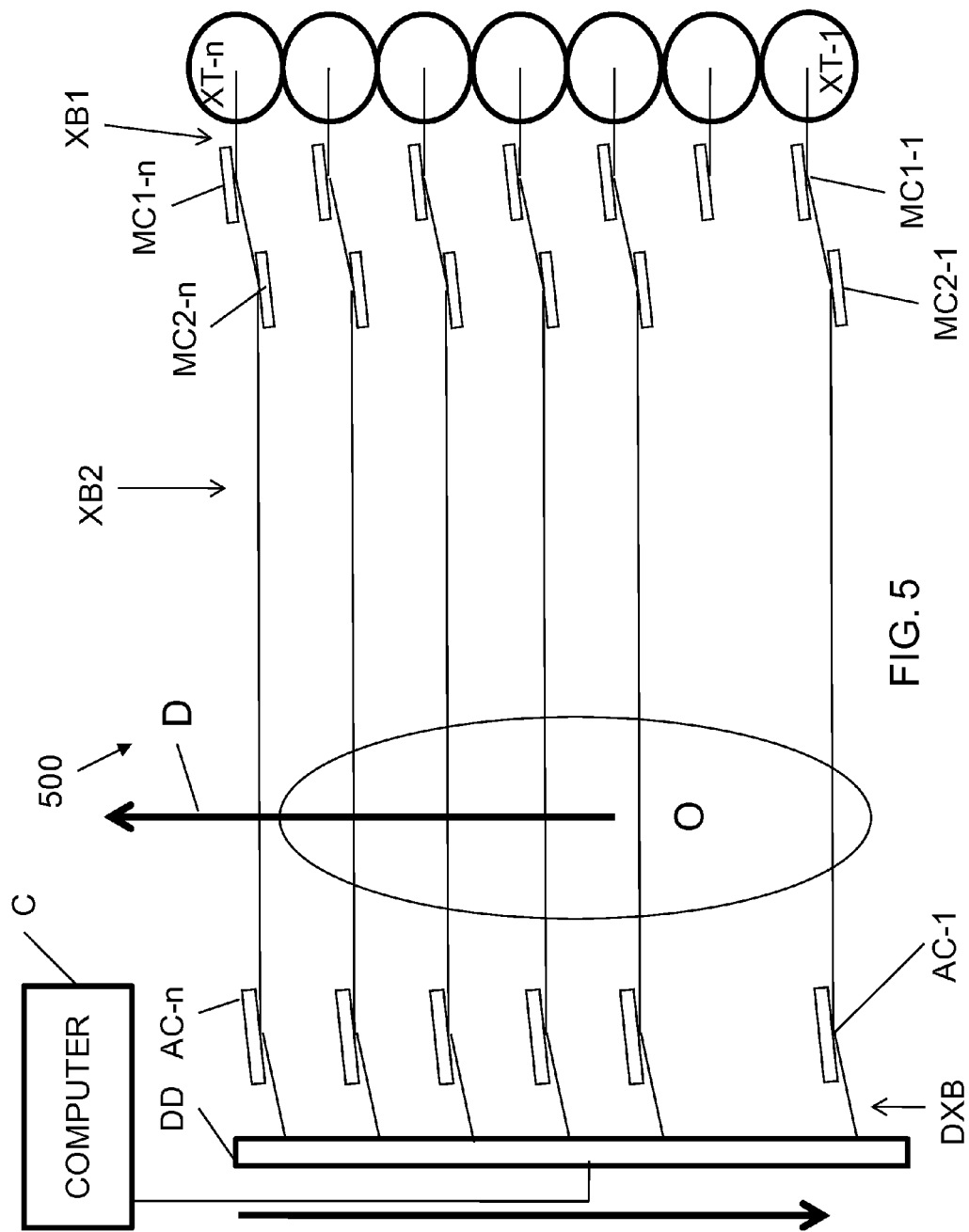

Referring now to FIG. 5, another example DEI system 500 for detecting an image of the object O according to an embodiment of the subject matter disclosed herein is shown. The DEI system 500 is similar to DEI system 100 shown in FIG. 1 except that DEI system 500 includes a second set of monochromator crystals MC2-1-MC2-n positioned downstream from a first set of monochromator crystals MC1-1-MC1-n.

Figure 6:
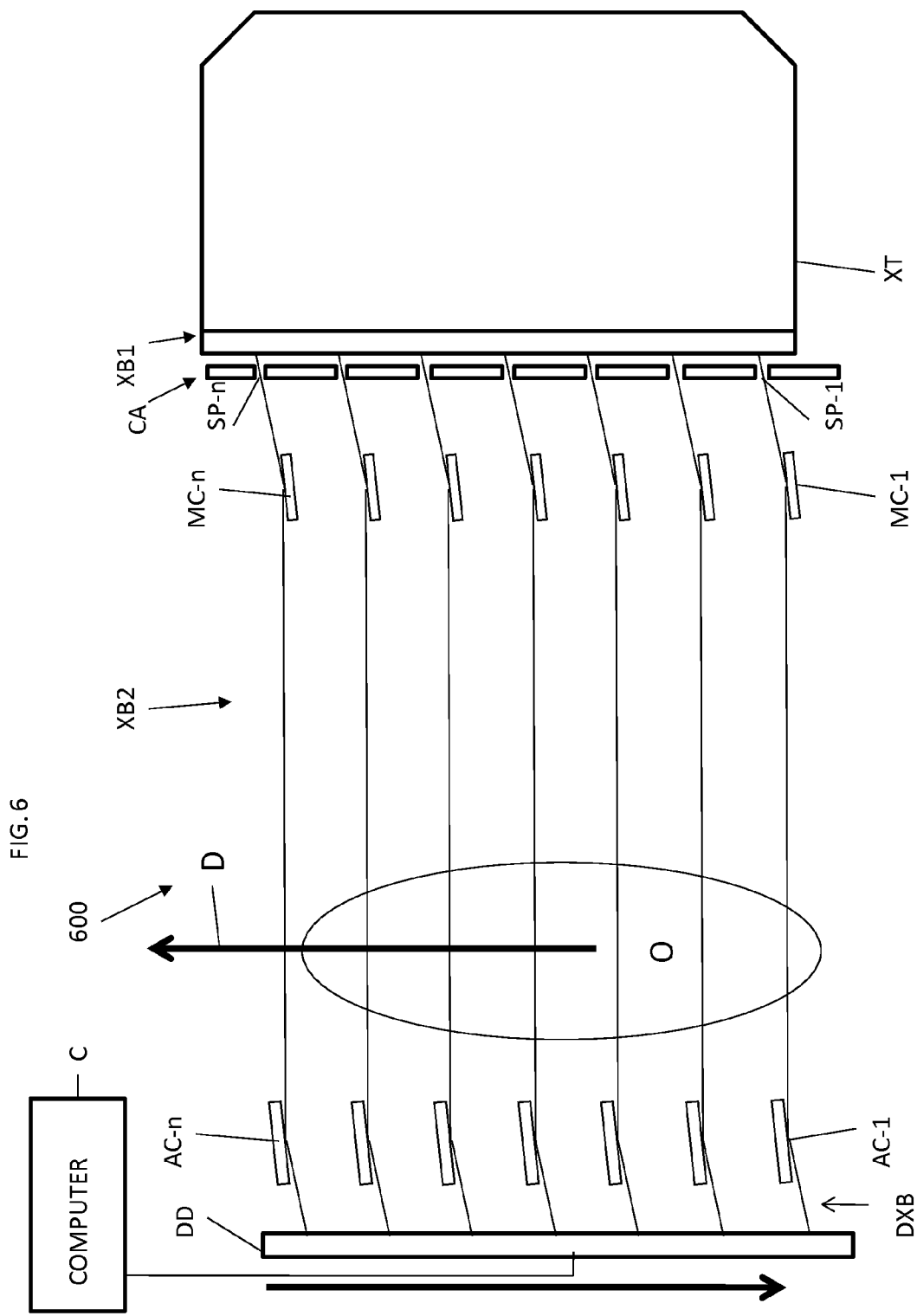

Referring now to FIG. 6, another example DEI system 600 for detecting an image of the object O according to an embodiment of the subject matter disclosed herein is shown. DEI system 600 is similar to DEI system 100 shown in FIG. 1 except that, rather than the use of multiple X-ray tubes XT-1-XT-N, system 600 includes a single X-ray tube XT having multiple source points SP-1-SP-n, each capable of functioning as a small area source. Therefore, X-ray tube XT can produce a plurality of X-ray beams, generally designated XB1.

The DEI system 600 shown in FIG. 6 also includes a collimator array CA, although the system may not include this component in another embodiment. Without the collimator array CA, the X-ray beams XB1 may be generated by small area sources at the X-ray tube XT. With the collimator array CA as shown in FIG. 6, a line beam, or even a large area X-ray beam produced by a large area X-ray beam source can be used in combination with the collimator array CA to generate a series of small area sources at the slits of the collimator array.

Figure 7:
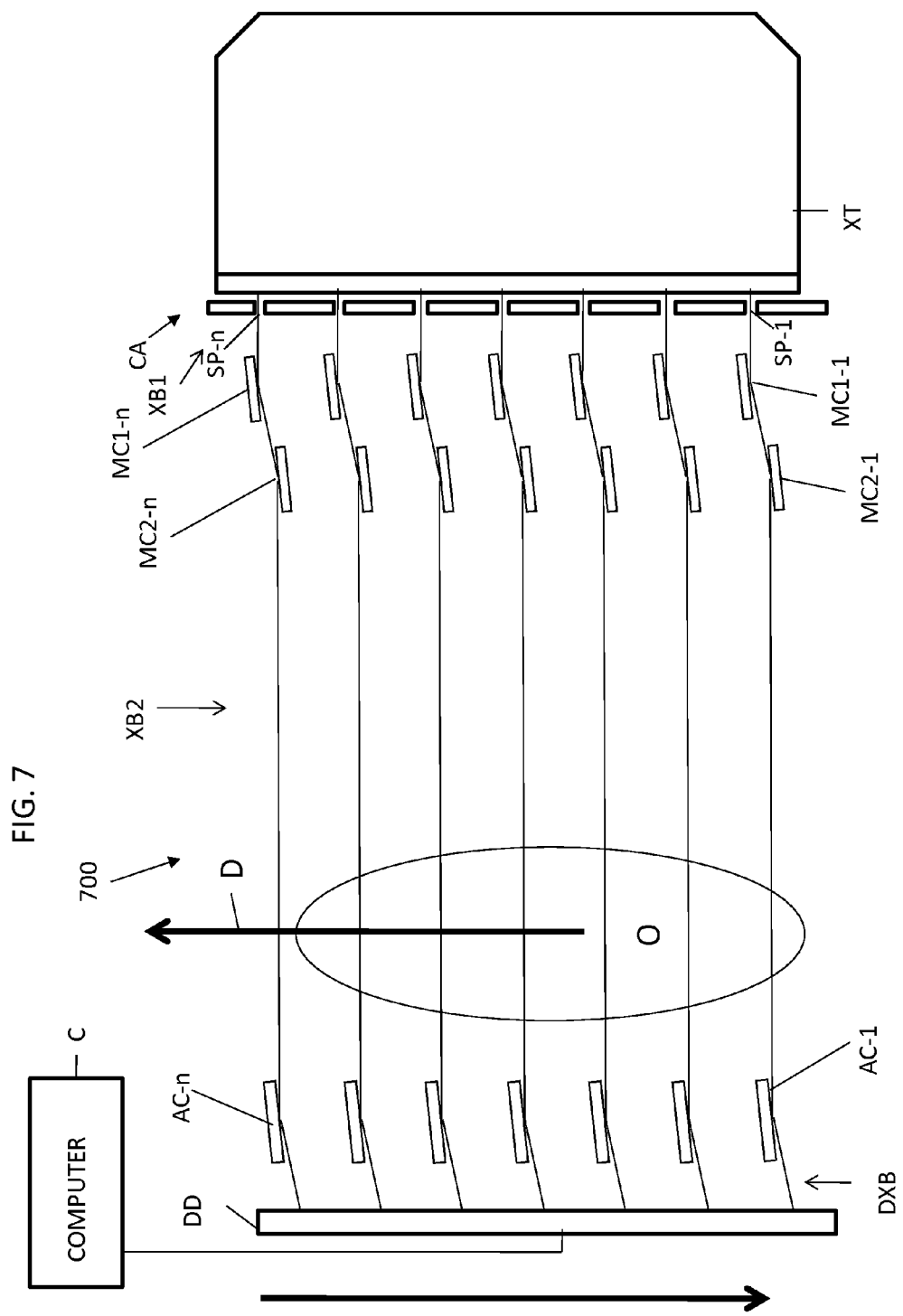

Referring now to FIG. 7, another example DEI system 700 for detecting an image of the object O according to an embodiment of the subject matter disclosed herein is shown. DEI system 700 is similar to DEI system 500 shown in FIG. 5 and DEI system 600 shown in FIG. 6. Similar to system 500 shown in FIG. 5, system 700 includes monochromator crystals MC1-1-MC1-n and MC2-1-MC2-n. Further, similar to system 600 shown in FIG. 6, system 700 includes a single X-ray tube XT having multiple source points SP-1-SP-n, each capable of functioning as a small area source for producing X-ray beams XB1. The system may include the collimator array CA or not as described with respect to FIG. 6.

Figure 8:
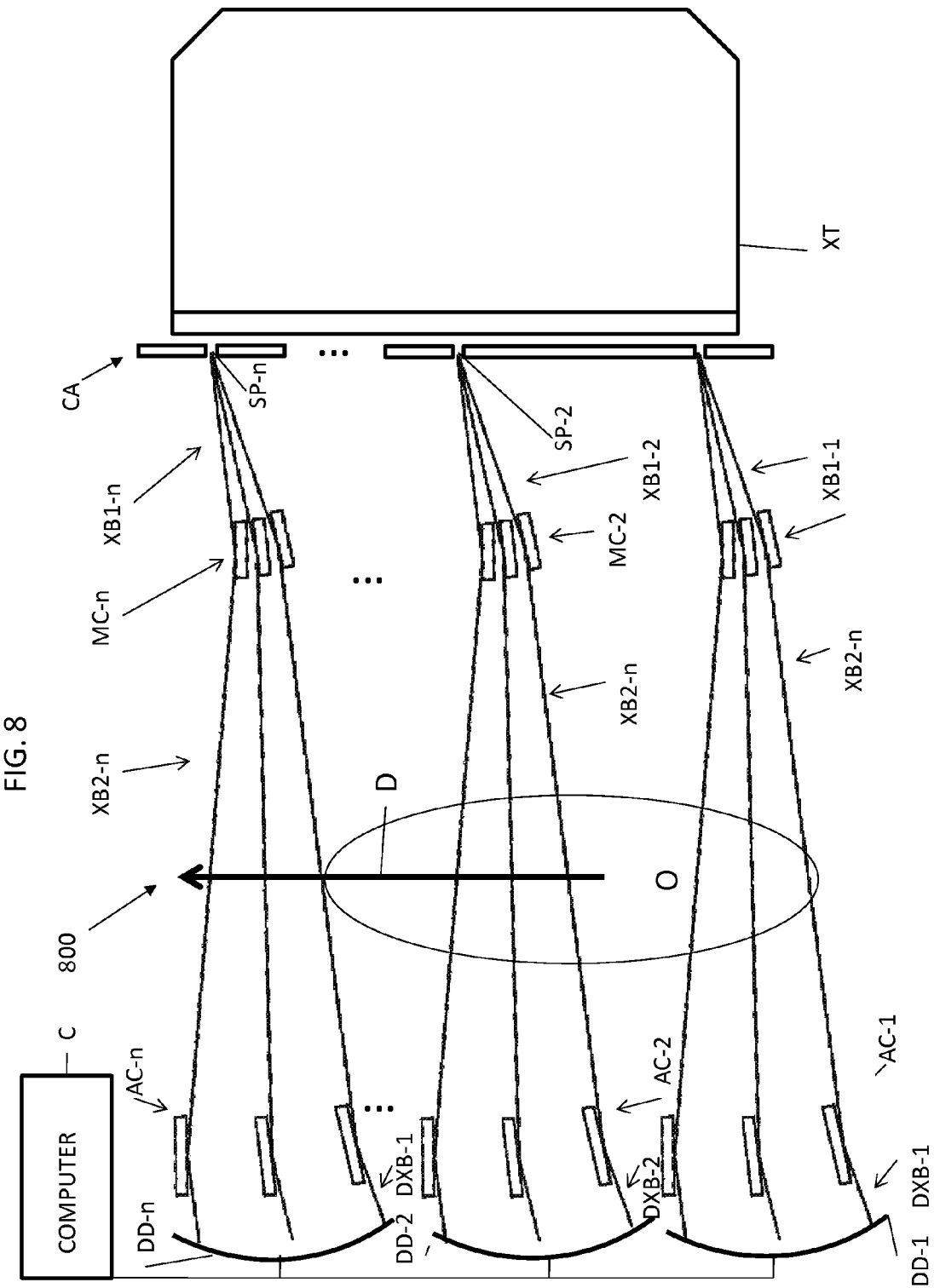

Referring now to FIG. 8, another example DEI system 800 for detecting an image of the object O according to an embodiment of the subject matter disclosed herein is shown. DEI system 800 is similar to DEI system 600 shown in FIG. 6 except that the source points SP-1-SP-n of system 800 each emit an X-ray beam XB that fans out toward sets of monochromator crystals MC-1-MC-n. For example, source points SP-1 and SP-n emit fanning X-ray beams, generally designated XB1-1 and XB1-n, respectively, directed to the sets of monochromator crystals MC-1 and MC-n, respectively. In turn, X-ray beam sets XB2-1-XB2-n, originating from the monochromator crystals, are directed towards the analyzer crystal sets AC-1-AC-n. The system may include the collimator array CA or not as described with respect to FIG. 6.

System 800 includes a plurality of digital detectors DD-1-DD-n each configured to receive respective, diffracted X-ray beams DXB-1-DXB-n from the analyzer crystal sets AC-1-AC-n. Computer C is operable to receive electrical signals from the digital detectors DD-1-DD-n for generating an image of the object O.

Figure 9:
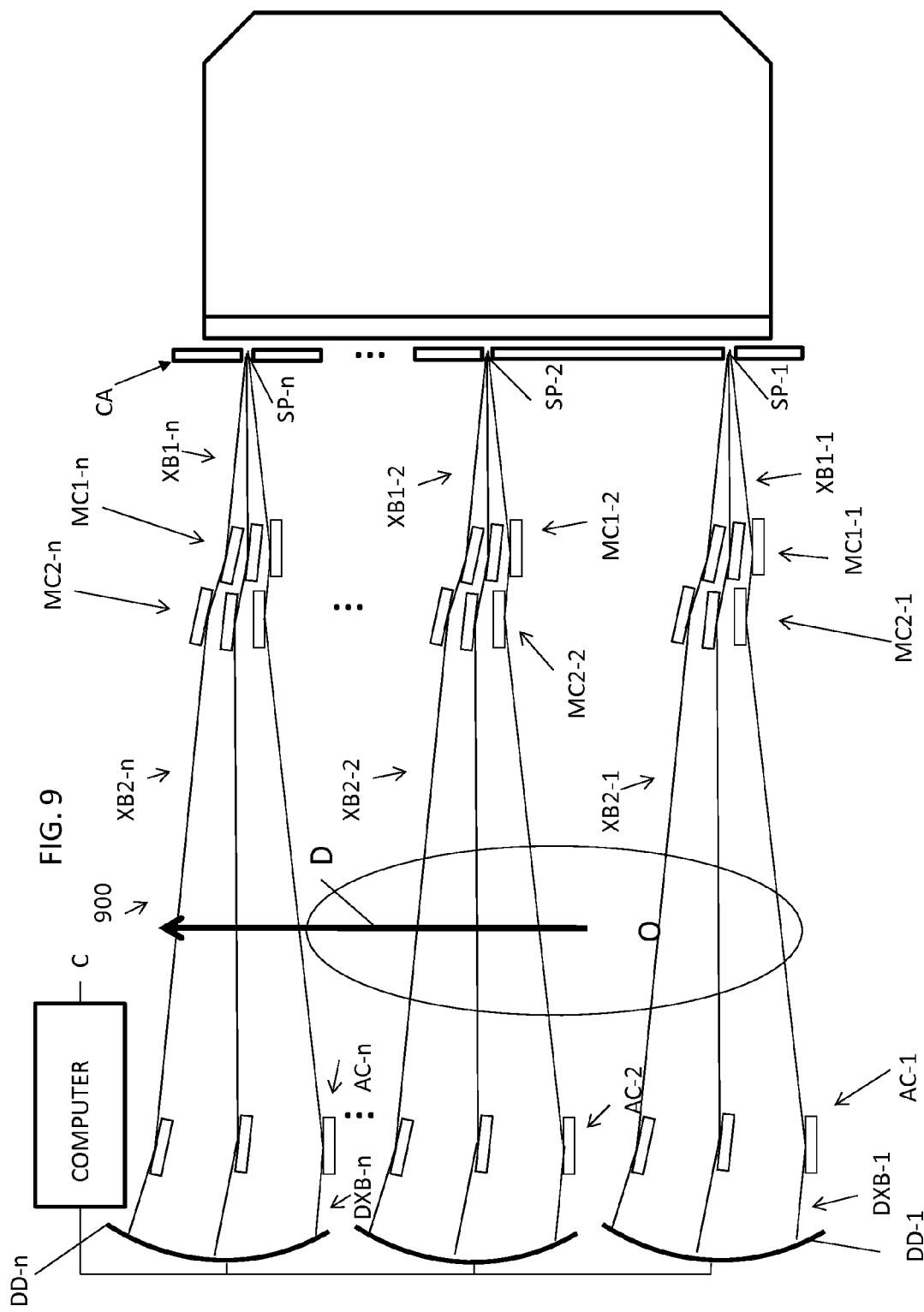

Referring now to FIG. 9, another example DEI system 900 for detecting an image of the object O according to an embodiment of the subject matter disclosed herein is shown. DEI system 900 is similar to DEI system 800 shown in FIG. 8 except that system 900 includes monochromator crystals MC1-1-MC1-n and MC2-1-MC2-n similar to DEI system 500 shown in FIG. 5. The system may include the collimator array CA or not as described with respect to FIG. 6.

Figure 10:
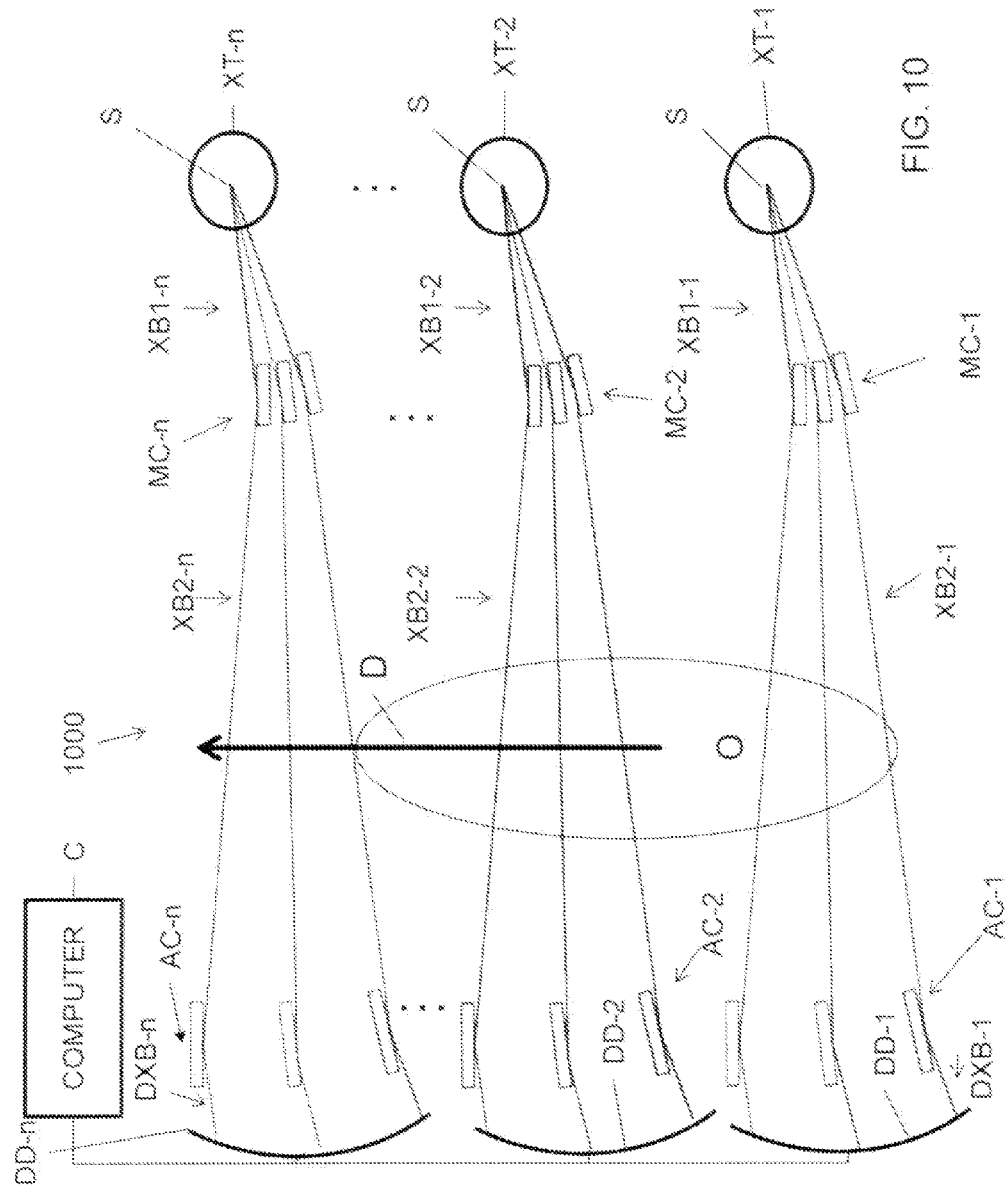

Referring now to FIG. 10, another example DEI system 1000 for detecting an image of the object O according to an embodiment of the subject matter disclosed herein is shown. DEI system 1000 is similar to DEI system 800 shown in FIG. 8 except that system 1000 includes X-ray tubes XT-1-XT-n similar to the DEI system 500 shown in FIG. 5.

Figure 11:
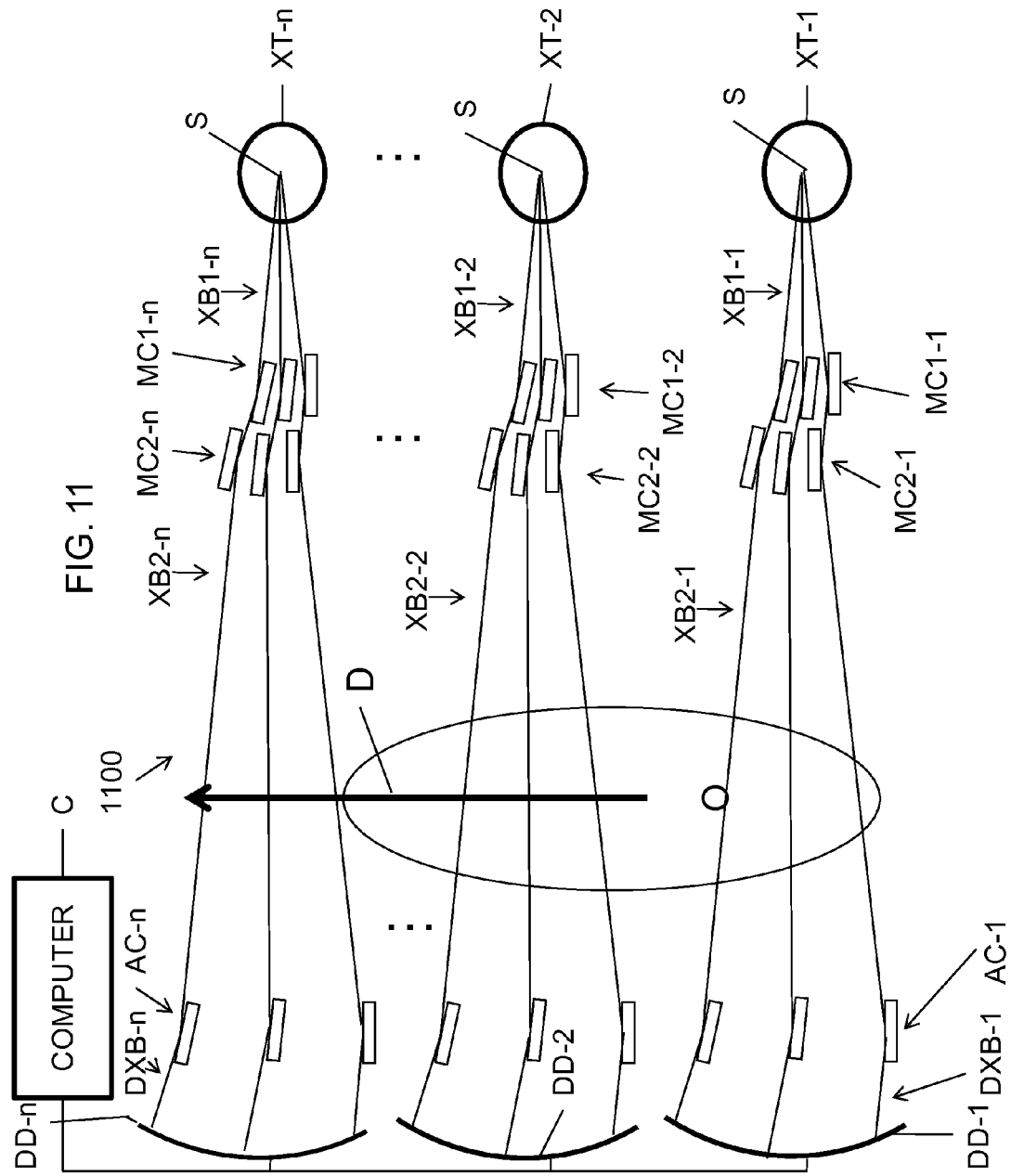

Referring now to FIG. 11, another example DEI system 1100 for detecting an image of the object O according to an embodiment of the subject matter disclosed herein is shown. DEI system 1100 is similar to DEI system 900 shown in FIG. 9 except that the source points originate from different X-ray tubes XT-1-XT-n similar to the DEI system 500 shown in FIG. 5.

Figure 12:
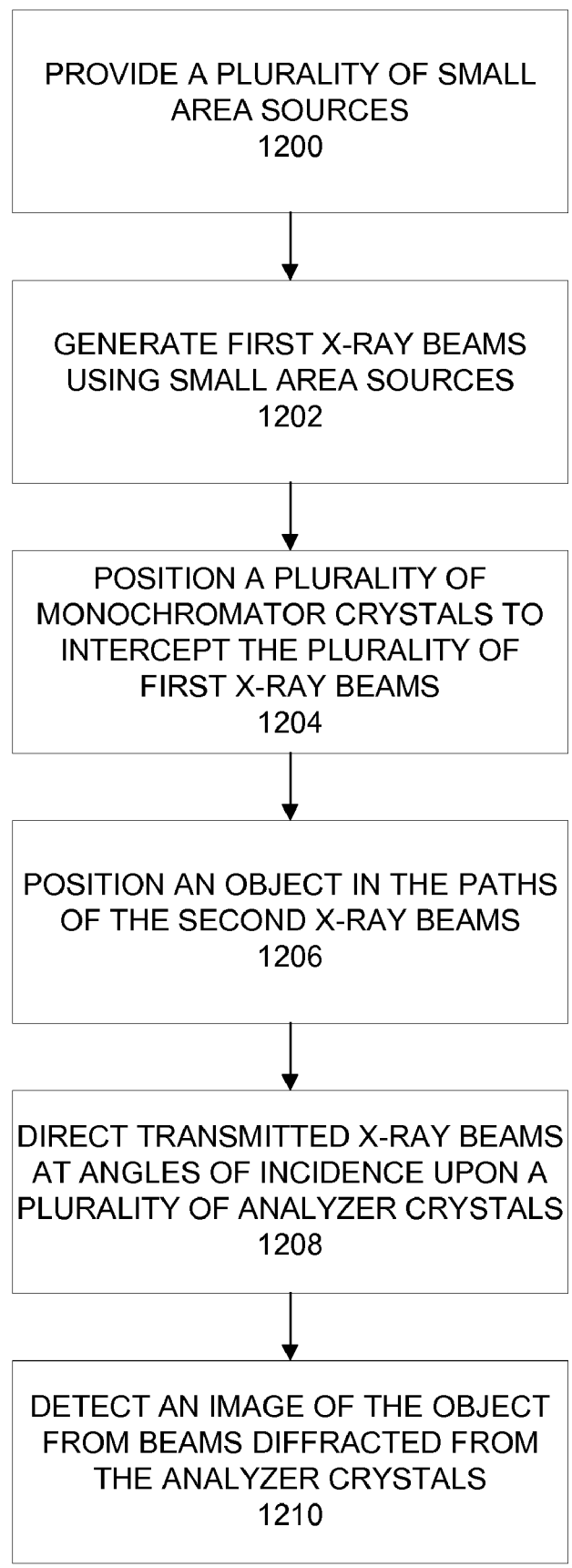
FIG. 12 is a flow chart of an exemplary process for imaging an object by use of a DEI system, such as one of the DEI systems shown in FIGS. 1-11, according to an embodiment of the subject matter described herein.

FIG. 12 is a flow chart illustrating an exemplary process for imaging object O by use of a DEI system, such as one of the DEI systems shown in FIGS. 1-11, according to an embodiment of the subject matter described herein. Referring to FIG. 12, in step 1200, a plurality of small area sources are provided. For example, the small area sources S of the X-ray tubes XT-1-XT-N shown in FIG. 1 may be provided in a DEI system.

In step 1202, a plurality of first X-ray beams may be generated using the small area sources. For example, the small area sources S of the X-ray tubes XT-1-XT-N shown in FIG. 1 may generate X-ray beams XB1.

A plurality of monochromator crystals, such as the monochromator crystals MC-1-MC-n shown in FIG. 1, may each be positioned to intercept a respective one of the first X-ray beams such that a plurality of second X-ray beams each having predetermined energy levels is produced (step 1204). For example, a surface of each of the monochromator crystals MC-1-MC-n shown in FIG. 1 can be positioned in the path of its respective X-ray beam for intercepting the beam. Each monochromator crystal can be adapted to reject the majority of photons of its respective X-ray beam that does not have a desired energy. Thus, a resulting second set of X-ray beams (e.g., X-ray beams XB2 shown in FIG. 1) can be produced that has a narrow range of X-ray energies. In one example, a surface of each monochromator crystal can be positioned at an angle of between about 5 degrees and 20 degrees with respect to a path of its respective X-ray beam incident upon the surface of the monochromator crystal. In this example, these angles may be used for [333] reflection. Alternatively, other suitable angles may be used in the positioning of the surface of monochromator crystal. In another example, a surface of each monochromator crystal can be positioned at an angle of between about 1 degree and 20 degrees with respect to a path of its respective X-ray beam incident upon the surface of monochromator crystal MC. If both [333] and [111] reflections are used, the angular range can be between about 1 degree and about 40 degrees for the energy range of 10 to 70 keV.

In step 1206, an object can be positioned in the paths of the second X-ray beams for transmission of the second X-ray beams through the object and emission from the object a plurality of transmission X-ray beams. For example, the object O shown in FIG. 1 can be positioned on a scanning stage for movement of the object O into the pathway of the second X-ray beams XB2.

In step 1208, the transmitted X-ray beam can be directed at angles of incidence upon analyzer crystals. For example, analyzer crystals AC-1-AC-n shown in FIG. 1 can be positioned in the paths of the transmitted X-ray beams and at an angle for intercepting the transmitted X-ray beams at angles of incidence. At least a portion of each beam intercepting a respective one of analyzer crystals AC-1-AC-n can be diffracted towards a detector, such as detector DD.

In step 1210, an image of object O can be detected from the beams diffracted from the analyzer crystal AC-1-AC-n. For example, detector DD can detect the diffracted beam from the analyzer crystals. The diffracted beams can be detected by one of the following exemplary detectors: a detector configured to digitize a detected image; a radiograph film; and an image plate. In one example, the image of an object can be detected from beam diffracted from analyzer crystals at a peak of a rocking curve of the analyzer crystals and/or near a peak of a rocking curve of the analyzer crystals. The detected image can be processed and presented to a user via a display of a computer.

Figure 13:
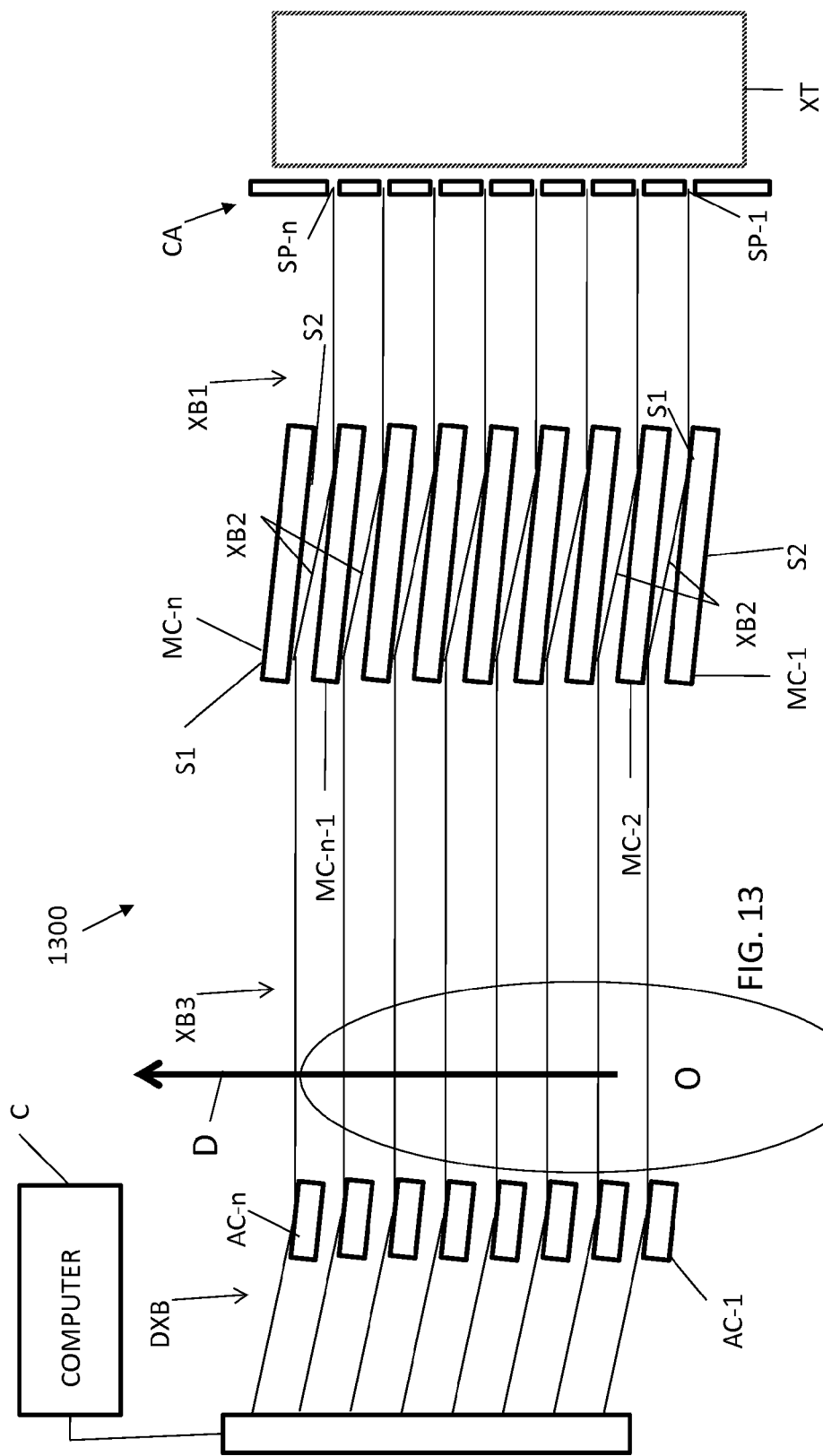
FIG. 13 is a schematic diagram of an example DEI system that can utilize facing sides of adjacent monochromator crystals for detecting an image of an object according to an embodiment of the subject matter described herein.

FIG. 13 is a schematic diagram of another example DEI system 1300 that can utilize facing sides of adjacent monochromator crystals for detecting an image of an object according to an embodiment of the subject matter described herein. The DEI system 1300 is similar to DEI system 600 shown in FIG. 6 except that the DEI system 1300 utilizes facing sides of adjacent monochromator crystals MC-1-MC-n for detecting an image of an object. For example, an X-ray generation device, such as X-ray tube XT, can generate multiple X-ray beams XB1 that are intercepted by sides S1 of monochromator crystals MC-1-MC-n–1 for producing a plurality of X-ray beams XB2. The X-ray beams XB2 are directed to sides S2 of monochromator crystals MC-2-MC-n for producing X-ray beams XB3, which can be substantially parallel to X-ray beams XB1. An object can pass through X-ray beams XB3, and the transmitted X-ray beams intercepted by analyzer crystals for downstream processing as described in further detail herein. The system may include the collimator array CA or not as described with respect to FIG. 6.

It is noted that a DEI system, such as the system shown in FIG. 13, can have more than two reflections on the monochromator crystals per X-ray beam. For example, an X-ray beam can be directed from a source to a side of a monochromator crystal for a first reflection towards a facing side of another monochromator crystal. The X-ray beam can then be reflected between the sides of the monochromator crystals for any number of times before the X-ray beam finally exits the monochromator crystals towards downstream DEI system components.

Figure 14:
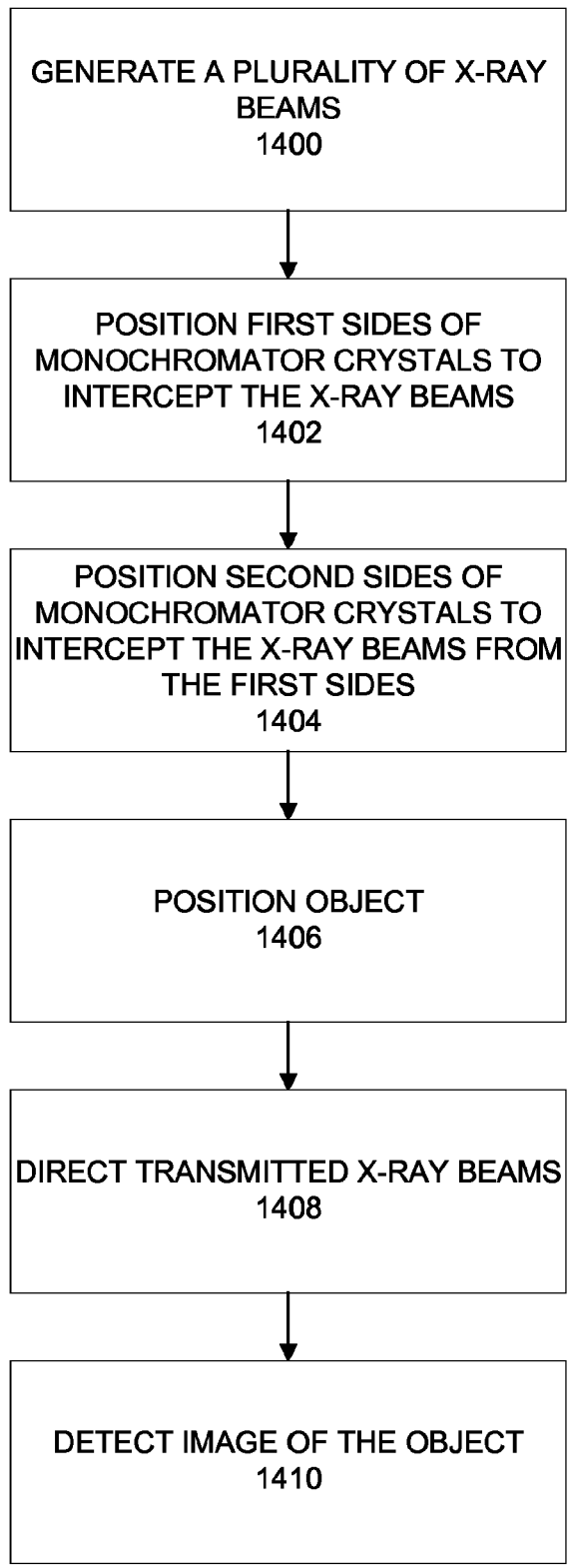
FIG. 14 is a flow chart of an exemplary process for imaging an object by use of a DEI system, such as one of the DEI system shown in FIG. 13, according to an embodiment of the subject matter described herein.

FIG. 14 is a flow chart illustrating an exemplary process for imaging an object by use of a DEI system, such as the DEI system 1300 shown in FIG. 13, according to an embodiment of the subject matter described herein. Referring to FIG. 14, in step 1400, a plurality of first X-ray beams may be generated by X-ray tube XT. Sides 51 of monochromator crystals MC-1-MC-n–1 are positioned to intercept a respective one of the first X-ray beams such that a plurality of second X-ray beams each having predetermined energy levels is produced (step 1402). For example, a surface S1 of each of the monochromator crystals can be positioned in the path of its respective X-ray beam for intercepting the beam. Each monochromator crystal can be adapted to reject the majority of photons of its respective X-ray beam that does not have a desired energy. Thus, a resulting second X-ray beam XB2 can be produced that has the predetermined energy level. In one example, a surface of each monochromator crystal can be positioned at an angle of between about 5 degrees and 20 degrees with respect to a path of its respective X-ray beam incident upon the surface of the monochromator crystal. In this example, these angles may be used for [333] reflection. Alternatively, other suitable angles may be used in the positioning of the surface of monochromator crystal. In another example, a surface of the monochromator crystal can be positioned at an angle of between about 1 degrees and 20 degrees with respect to a path of its respective X-ray beam incident upon the surface of the monochromator crystal. In another example, a surface of each monochromator crystal can be positioned at an angle of between about 1 degree and 20 degrees with respect to a path of its respective X-ray beam incident upon the surface of monochromator crystal MC. If both [333] and [111] reflections are used, the angular range can be between about 1 degree and about 40 degrees for the energy range of 10 to 70 keV.

In step 1404, the second sides S2 of the monochromator crystals MC-2-MC-n are positioned to intercept the second X-ray beams XB2 for producing the third X-ray beams, generally designated XB3. An object O can be positioned in the paths of the third X-ray beams XB3 for transmission of the third X-ray beams XB3 through the object and emission from the object transmission X-ray beams (step 1406).

In step 1408, the transmitted X-ray beams can be directed at angles of incidence upon the analyzer crystals AC-1-AC-n. Further, in step 1410, an image of the object can be detected from the diffracted X-ray beams DXB.

In another example of detecting the image of the object, a first angle image of object can be detected from first diffracted beams emitted from analyzer crystals positioned at a first angular position. The first angle image of the object can be detected at a low rocking curve angle setting of the analyzer crystals. Further, a second angle image of the object can be detected from a second diffracted beam emitted from analyzer crystals positioned at a second angular position. The second angle image of the object can be detected at a high rocking curve angle setting of the analyzer crystals. The first and second angle images can be combined by a computer to derive a refraction image and apparent absorption image. Further, the computer can derive a mass density image of the object from the refraction image. The mass density image can be presented to a user via a display of the computer.

Figure 15:
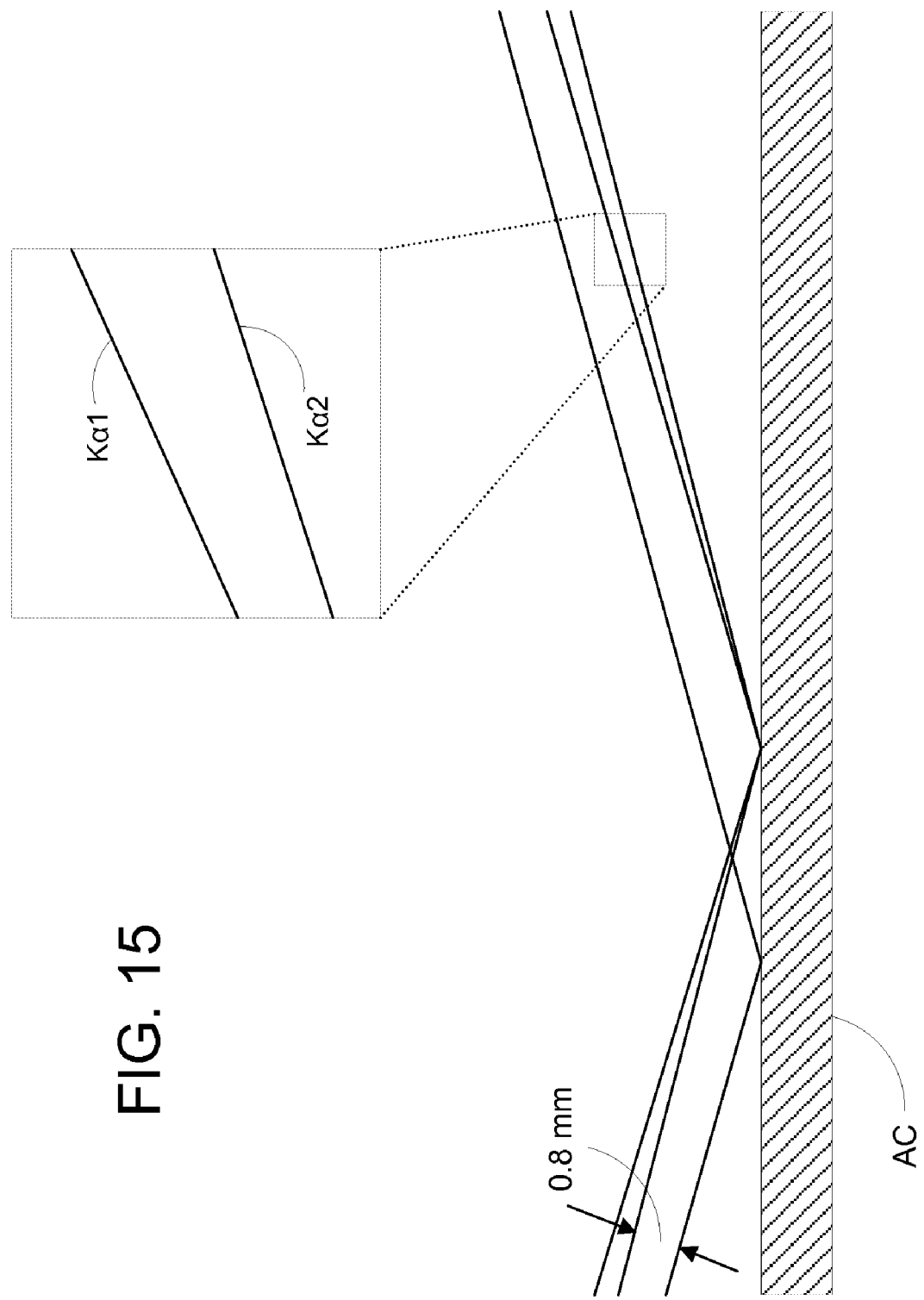
FIG. 15 is a side view of an analyzer crystal of any one of the DEI systems shown in FIGS. 1-11 and 13 according to an embodiment of the subject matter described herein.

FIG. 15 is a side view of an analyzer crystal AC of any one of the DEI systems shown in FIGS. 1-11 and 13 according to an embodiment of the subject matter described herein. Referring to FIG. 15, the diffraction of characteristic emission lines $K\alpha 1$ and $K\alpha 2$ from the surface of analyzer crystal AC are shown. The accommodation of more than one x-ray energy can result in improved X-ray flux.

In another embodiment, a DEI system in accordance with the subject matter described herein can include a mismatch crystal design for rejecting particular X-rays emitted by an X-ray tube. In this design, the $K\alpha 2$ emission line of the X-ray beam can be eliminated at the monochromator. A collimator can be positioned for blocking a portion of an X-ray beam that fall outside an angular acceptance window of a first set of monochromator crystals, such as, for example, one of monochromator crystals MC1-1-MC1-n shown in FIG. 5. The unblocked portion of the X-ray beam can intercept the first monochromator crystals, which refract the unblocked portions in a direction for intercept by a second set of monochromator crystals, such as, for example, one of monochromator crystals MC2-1-MC2-n shown in FIG. 5. The first set of monochromator crystals can be tuned to a particular angle using Bragg's Law to select a very narrow range of photon energies for resulting in diffracted monochromatic beams directed towards the second set of monochromator crystals. Because of the divergence of the X-ray beam from a source point, the first set of monochromator crystals can diffract a range of energies which can include the characteristic emission lines $K\alpha 1$ and $K\alpha 2$ and bremsstrahlung radiation at nearby energies. A function of the second set of monochromator crystals is to redirect the beam to a direction parallel to the incident beam and aligned with a set of analyzer crystals, such as, for example, analyzer crystals AC-1-AC-n shown in FIG. 5. When tuning the system for a particular energy, the monochromator crystals of the first set are aligned first, and then the monochromator crystals of the second set are tuned to find the position of the beam.

The monochromator crystals of the first and second sets can be configured in a mismatch crystal design for rejecting particular X-ray beams emitted by source points, such as small area sources of an X-ray tube. The monochromator crystals can be used to eliminate the $K\alpha 2$ emission line of the X-ray beam, which can be achieved by utilizing the angular acceptance versus energy for different crystals. In one example, the monochromator crystals can be germanium [333] and silicon [333] monochromator crystals, respectively.

In another example of detecting the image of the object, first angle image of an object can be detected from first diffracted beams emitted from analyzer crystals positioned at first angular positions. The first angle image of an object can be detected at a low rocking curve angle setting of the analyzer crystals. Further, a second angle image of the object can be detected from second diffracted beams emitted from analyzer crystals positioned at second angular positions. The second angle images of the object can be detected at a high rocking curve angle setting of the analyzer crystals. The first and second angle images can be combined by a computer to derive a refraction image. Further, the computer can derive a mass density image of the object from the refraction image. The mass density image can be presented to a user via a display of the computer.

Exemplary Applications

The systems and methods in accordance with the subject matter described herein can be applied to a variety of medical applications. As set forth above, the systems and methods described herein can be applied for breast imaging. Further, for example, the systems and methods described herein can be applied to cartilage imaging, neuroimaging, cardiac imaging, vascular imaging (with and without contrast), pulmonary (lung) imaging, bone imaging, genitourinary imaging, gastrointestinal imaging, soft tissue imaging in general, hematopoietic system imaging, and endocrine system imaging. In addition to image time and dose, a major advancement of using higher energy X-rays is the thickness of the object that can be imaged. For applications such as breast imaging, the system described allows for imaging full thickness breast tissue with a clinically realistic imaging time. The same can be said for other regions of the body, such as the head, neck, extremities, abdomen, and pelvis. Without the limitations of X-ray absorption, utilization of DEI with higher energy X-rays dramatically increases the penetration ability of X-rays. For soft tissue, only a small portion of the X-ray photons incident on the object are absorbed, which greatly increases efficiency of emitted photons from the X-ray tube reaching the detector.

With respect to pulmonary imaging, DEI techniques as described herein can produce excellent contrast in the lungs and can be used heavily for diagnosing pulmonary conditions such as pneumonia. Fluid collections in the lungs generate a marked density gradient that could be detected easily with DEI. The density gradient, characteristics of the surrounding tissue, and geometric differences between normal lung tissue and tissue with a tumor can be large, producing good contrast. Further, DEI techniques described herein can be applied to lung cancer screening and diagnosis.

With respect to bone imaging, DEI techniques as described herein can produce an excellent image of bone in general. High refraction and extinction contrast of DEI can be especially useful for visualizing fractures and lesions within the bone.

Further, the systems and methods in accordance with the subject matter described herein can be applied to a variety of inspection and industrial applications. For example, the systems and methods can be applied for meat inspection, such as poultry inspection. For example, the systems and methods can be used for viewing sharp bones, feathers, and other low contrast objects in meats that required screening and/or removal. The systems and methods described herein can be applied for such screening.

The systems and methods described herein can also be applied for manufacture inspection. For example, the systems and methods can be used for inspecting welds, such as in aircraft production. DEI techniques as described herein can be used to inspect key structural parts that undergo heavy wear and tear, such as jet turbine blades. Further, for example, the systems and methods described herein can be used for inspecting circuit boards and other electronics. In another example, the systems and methods described herein can be used for tire inspection, such as the inspection of steel belts and tread integrity.

Further, the systems and methods in accordance with the subject matter described herein can be used for security screening purposes. For example, the systems and methods can be used for screening at airports and seaports. DEI techniques as described herein can be used for screening for plastic and low absorption contrast objects, such as plastic knives, composite guns difficult to detect with conventional X-ray, and plastic explosives. For imaging larger objects, such is for airport baggage inspection, the distance between the X-ray tube and detector can be increased to allow beam divergence. A larger analyzer crystal would be necessary to accommodate a larger fan beam.

The device described provides a mechanism that can be translated into a computed tomography imaging system, or DEI-CT. A DEI-CT system, resembling a third generation conventional computed tomography system, would use the same apparatus but modified for rotation around a central point. Alternatively, the system could remain stationary and the object, sample, or patient could be rotated in the beam. A DEI-CT system of this design would produce images representing X-ray absorption, refraction, and ultra-small angle scatter rejection (extinction), but they would be resolved in three dimensions.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the subject matter disclosed herein. In the case of program code execution on programmable computers, the computer will generally include a processor, a storage medium readable by the processor (including volatile and non-volatile memory and/or storage elements), at least one input device and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the subject matter disclosed herein. When implemented on a general-purpose processor, the program code combines with the processor to provide a unique apparatus that operates to perform the processing of the presently disclosed subject matter.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A method for detecting an image of an object, the method comprising:
   providing a plurality of small area X-ray sources;
   generating a plurality of first X-ray beams using the plurality of small area sources;
   positioning a plurality of monochromator crystals to intercept the plurality of first X-ray beams such that a plurality of second X-ray beams, each having predetermined energy levels, is produced;
   positioning an object in paths of the plurality of second x-ray beams for transmission of the plurality of second X-ray beams through the object and emitting from the object a plurality of transmitted X-ray beams;
   directing the plurality of transmitted X-ray beams at angles of incidence upon a plurality of analyzer crystals; and
   detecting an image of the object from a plurality of beams diffracted from the plurality of analyzer crystals.

2. The method of claim 1 wherein providing the plurality of small area sources comprises providing a single X-ray tube having multiple small area sources.

3. The method of claim 1 wherein providing the plurality of small area sources comprises providing a plurality of X-ray tube sources for generating the plurality of first X-ray beams.

4. The method of claim 1 wherein providing the plurality of small area sources comprises providing a collimator array adjacent a large area X-ray beam source.

5. The method of claim 1 wherein providing the plurality of small area sources comprises providing a collimator array adjacent an X-ray line source.

6. The method of claim 1 wherein the small area sources are spaced apart from each other.

7. The method of claim 6 wherein the small area sources are substantially linearly arranged, and wherein the spacing of adjacent small area sources is substantially equal.

8. The method of claim 7 wherein the spacing of adjacent small area sources is 0.5 cm to 25 cm.

9. The method of claim 1 wherein generating the plurality of first X-ray beams comprises generating X-ray beams having a characteristic X-ray energy ranging from 10 keV to 70 keV.

10. The method of claim 1 wherein positioning the plurality of monochromator crystals comprises positioning surfaces of the monochromator crystals at angles of between 1 degree and 40 degrees with respect to paths of the first X-ray beams incident upon the surfaces of the monochromator crystals.

11. The method of claim 1 wherein each of the monochromator crystals are matched in orientation and lattice planes to a respective one of the analyzer crystals.

12. The method of claim 1 wherein the monochromator crystals are symmetric crystals.

13. The method of claim 12 wherein the monochromator crystals are silicon crystals.

14. The method of claim 13 wherein the silicon crystals have one of [111] and [333]reflection.

15. The method of claim 1 wherein the analyzer crystals are Bragg type crystals.

16. The method of claim 1 wherein the object is a soft tissue object.

17. The method of claim 16 wherein the soft tissue object is breast tissue.

18. The method of claim 1 wherein the second X-ray beams apply a total radiation dosage of less than or equal to about 0.5 mrad to the object.

19. The method of claim 1 wherein the detector is configured to produce a digitized image of the object.

20. The method of claim 1 wherein the detector is one of a radiographic film and an image plate.

21. The method of claim 1 wherein detecting the image of the object includes detecting the image of the object from the beam diffracted from the analyzer crystals one of at or near a peak of a rocking curve of the analyzer crystal.

22. The method of claim 21 wherein the one of at and near the peaks occurs approximately one-half of a Darwin width of the rocking curve.

23. The method of claim 1 wherein detecting the image of the object comprises:
   detecting a first angle image of the object from first diffracted beams emitted from the analyzer crystals positioned at first angular positions;
   detecting a second angle image of the object from second diffracted beams emitted from the analyzer crystals positioned at second angular positions;
   combining the first and second angle images to derive a refraction and apparent absorption image; and
   deriving a mass density image of the object from the refraction image.

24. The method of claim 23 wherein detecting the first angle image comprises detecting the first angle image of the object from the analyzer crystals at a low rocking curve angle setting of the analyzer crystals, and wherein detecting the second angle image comprises detecting the second angle image of the object from the analyzer crystals at a high rocking curve angle setting of the analyzer crystals.

25. The method of claim 1 wherein the monochromator crystals are spaced apart from each other.

26. The method of claim 25 wherein the monochromator crystals are substantially linearly arranged, and wherein the spacing of adjacent monochromator crystals is substantially equal.

27. The method of claim 26 wherein the spacing of adjacent monochromator crystals is 0.5 cm to 25 cm.

28. The method of claim 1 wherein the plurality of monochromator crystals is a plurality of first monochromator crystals, and wherein the method further comprises positioning a plurality of second monochromator crystals to intercept the second X-ray beams and to direct the second X-ray beams towards the analyzer crystals.

29. The method of claim 28 wherein positioning the plurality of second monochromator crystals comprises positioning the plurality of second monochromator crystals such that the second X-ray beams are directed along paths substantially parallel to paths of the first X-ray beams.

30. The method of claim 29 using the first monochromator crystals and the second monochromator crystals for rejecting predetermined portions of the first X-ray beams.

31. A system for detecting an image of an object, the system comprising:
   a plurality of small area sources configured to generate a plurality of first X-ray beams;
   a plurality of monochromatic crystals positioned in predetermined positions to directly intercept the plurality of first X-ray beams and wherein a plurality of second X-ray beams is produced for transmission through an object;
   a plurality of analyzer crystals positioned to intercept a plurality of transmitted X-ray beams at angles of incidence of the plurality of analyzer crystals; and
   an image detector configured to detect an image of the object from a plurality of beams diffracted from the plurality of analyzer crystals.

32. The system of claim 31 wherein the plurality of small area sources comprises one of a single X-ray tube and a plurality of X-ray tube sources.

33. The system of claim 31 further comprising: a large area X-ray source and a collimator array positioned adjacent to the large area X-ray source.

34. The system of claim 31 wherein the small area sources are spaced apart from each other.

35. The system of claim 34 wherein the small area sources are substantially linearly arranged, and wherein the spacing of adjacent small area sources is substantially equal.

36. The system of claim 35 wherein the spacing of adjacent small area sources is 0.5 cm to 25 cm.

37. The system of claim 31 wherein the first X-ray beams have a characteristic X-ray energy ranging from about 10 keV to about 70 keV.

38. The system of claim 31 wherein surfaces of the monochromator crystals are positioned at angles of between about 1 degree and 40 degrees with respect to paths of the first X-ray beams incident upon the surfaces of the monochromator crystals.

39. The system of claim 31 wherein each of the monochromator crystals are matched in orientation and lattice planes to a respective one of the analyzer crystals.

40. The system of claim 31 wherein the monochromator crystals are symmetric crystals.

41. The system of claim 40 wherein the monochromator crystals are silicon crystals.

42. The system of claim 41 wherein the silicon crystals have [333] reflection.

43. The system of claim 31 wherein the analyzer crystals are Bragg type crystals.

44. The system of claim 31 wherein the object is a soft tissue object.

45. The system of claim 44 wherein the soft tissue object is breast tissue.

46. The system of claim 31 wherein the second X-ray beams apply a total radiation dosage of less than or equal to about 0.5 mrad to the object.

47. The system of claim 31 wherein the image detector is configured to receive the diffracted beams.

48. The system of claim 47 wherein the image detector is configured to produce a digitized image of the object.

49. The system of claim 47 wherein the image detector is a radiographic film.

50. The system of claim 47 wherein the image detector is an image plate.

51. The system of claim 47 wherein the image detector is configured to detect the image of the object from the beam diffracted from the analyzer crystals one of at or near a peak of a rocking curve of the analyzer crystal.

52. The system of claim 51 further comprising a computer configured to derive at least one of a diffraction enhanced image, an absorption image, a refraction image, a scatter image, and a mass density image of the object from the detected image.

53. The system of claim 51 wherein the one of at and near the peaks occurs approximately one-half of a Darwin width of the rocking curve.

54. The system of claim 31 wherein the image detector is configured to:
   detect a first angle image of the object from first diffracted beams emitted from the analyzer crystals positioned at first angular positions; and
   detect a second angle image of the object from second diffracted beams emitted from the analyzer crystals positioned at second angular positions; and wherein the system further comprises a computer configured to:
combine the first and second angle images to derive a refraction and apparent absorption image; and
derive a mass density image of the object from the refraction image.

55. The system of claim 54 wherein the image detector is configured to detect the first angle image of the object from the analyzer crystals at a low rocking curve angle setting of the analyzer crystals, and wherein the image detector is configured to detect the second angle image comprises detecting the second angle image of the object from the analyzer crystals at a high rocking curve angle setting of the analyzer crystals.

56. The system of claim 31 wherein the monochromator crystals are spaced apart from each other.

57. The system of claim 56 wherein the monochromator crystals are substantially linearly arranged, and wherein the spacing of adjacent monochromator crystals is substantially equal.

58. The system of claim 57 wherein the spacing of adjacent monochromator crystals is 0.5 cm to 25 cm.

59. The system of claim 31 wherein the plurality of monochromator crystals is a plurality of first monochromator crystals, and wherein the system further comprises a plurality of second monochromator crystals positioned to intercept the second X-ray beams and to direct the second X-ray beams towards the analyzer crystals.

60. The system of claim 59 wherein the plurality of second monochromator crystals are positioned such that the second X-ray beams are directed along paths substantially parallel to paths of the first X-ray beams.

61. The system of claim 59 wherein the first monochromator crystals are mismatched with the second monochromator crystals.

62. The system of claim 59 wherein the first monochromator crystals and the second monochromator crystals are selected for rejecting predetermined portions of the first X-ray beams.

63. The system of claim 59 wherein the first monochromator crystals and the second monochromator crystals are one of germanium and silicon monochromator crystals.

64. The system of claim 59 wherein the first monochromator crystals and the second monochromator crystals are one of germanium [333] and silicon [333] monochromator crystals.

65. The system of claim 31 comprising a computer configured for adjusting a radiation dose applied by the second X-ray beams to the object.

66. A method for detecting an image of an object, the method comprising:
generating a plurality of first X-ray beams;
positioning a plurality of monochromator crystals to intercept the plurality of first X-ray beams on first sides of the plurality of monochromator crystals for producing a plurality of second X-ray beams;
positioning second sides of the plurality of monochromator crystals to intercept the plurality of second X-ray beams such that a plurality of third X-ray beams, each having predetermined energy levels, is produced;
positioning an object in paths of the plurality of third x-ray beams for transmission of the plurality of third X-ray beams through the object and emitting from the object a plurality of transmitted X-ray beams;
directing the plurality of transmitted X-ray beams at angles of incidence upon a plurality of analyzer crystals; and
detecting an image of the object from a plurality of beams diffracted from the plurality of analyzer crystals.

67. The method of claim 66 wherein generating the plurality of first X-ray beams comprises using at least one X-ray tube source for generating the plurality of first X-ray beams.

68. The method of claim 66 wherein generating the plurality of first X-ray beams comprises generating X-ray beams having a characteristic X-ray energy ranging from 10 keV to about 70 keV.

69. The method of claim 66 wherein each of the monochromator crystals are matched in orientation and lattice planes to a respective one of the analyzer crystals.

70. The method of claim 66 wherein the monochromator crystals are symmetric crystals.

71. The method of claim 70 wherein the monochromator crystals are silicon crystals.

72. The method of claim 71 wherein 7 silicon crystals have [333] reflection.

73. The method of claim 66 wherein the analyzer crystals are Bragg type crystals.

74. The method of claim 66 wherein the object is a soft tissue object.

75. The method of claim 74 wherein the soft tissue object is breast tissue.

76. The method of claim 66 wherein the third X-ray beams apply a total radiation dosage of less than or equal to about 0.5 mrad to the object.

77. The method of claim 66 wherein detecting image of the object comprises receiving the diffracted beams at a detector.

78. The method of claim 77 wherein the detector is configured to produce a digitized image of the object.

79. The method of claim 77 wherein the detector is a radiographic film.

80. The method of claim 77 wherein the detector is an image plate.

81. The method of claim 66 wherein detecting the image of the object includes detecting the image of the object from the beam diffracted from the analyzer crystals one of at or near a peak of a rocking curve of the analyzer crystal.

82. The method of claim 81 comprising deriving at least one of a diffraction enhanced image, an absorption image, a refraction image, a scatter image, and a mass density image of the object from the detected image.

83. The method of claim 81 wherein the one of at and near the peaks occurs approximately one-half of a Darwin width of the rocking curve.

84. The method of claim 66 wherein detecting the image of the object comprises:
detecting a first angle image of the object from first diffracted beams emitted from the analyzer crystals positioned at first angular positions;
detecting a second angle image of the object from second diffracted beams emitted from the analyzer crystals positioned at second angular positions;
combining the first and second angle images to derive a refraction and apparent absorption image; and
deriving a mass density image of the object from the refraction image.

85. The method of claim 84 wherein detecting the first angle image comprises detecting the first angle image of the object from the analyzer crystals at a low rocking curve angle setting of the analyzer crystals, and wherein detecting the second angle image comprises detecting the second angle image of the object from the analyzer crystals at a high rocking curve angle setting of the analyzer crystals.

86. The method of claim 66 wherein the monochromator crystals are spaced apart from each other.

87. The method of claim 86 wherein the monochromator crystals are substantially linearly arranged, and wherein the spacing of adjacent monochromator crystals is substantially equal.

88. The method of claim 86 wherein the spacing of adjacent monochromator crystals is 0.5 cm to 25 cm.

89. The method of claim 66 wherein positioning the second sides of the monochromator crystals comprises positioning the second sides of the monochromator crystals such that the third X-ray beams are directed along paths substantially parallel to paths of the first X-ray beams.

90. The method of claim 66 wherein the monochromator crystals are one of germanium and silicon monochromator crystals.

91. The method of claim 66 wherein the monochromator crystals are one of germanium [333] and silicon [333] monochromator crystals.

92. The method of claim 66 comprising adjusting a radiation dose applied by the third X-ray beams to the object.

93. The method of claim 66 wherein the first side opposes the second side on a same monochromator crystal.

94. The method of claim 93 wherein the first side of the monochromator crystals is parallel to the second side of adjacent monochromator crystals.

95. A system for detecting an image of an object, the system comprising:
   an X-ray generation device configured to generate a plurality of first X-ray beams;
   a plurality of monochromatic crystals including first and second sides, wherein the first sides are positioned in predetermined positions to directly intercept the plurality of first X-ray beams for generating a plurality of second X-ray beams, wherein the second sides are positioned to intercept the plurality of second X-ray beams, and wherein a plurality of third X-ray beams is produced for transmission through an object;
   a plurality of analyzer crystals positioned to intercept a plurality of transmitted X-ray beams at angles of incidence of the analyzer crystals; and
   an image detector configured to detect an image of the object from a plurality of beams diffracted from the plurality of analyzer crystals.

96. The system of claim 95 wherein the X-ray generation device comprises a single X-ray tube.

97. The system of claim 95 wherein the first X-ray beams have a characteristic X-ray energy ranging from about 10 keV to about 70 keV.

98. The system of claim 95 wherein each of the monochromator crystals are matched in orientation and lattice planes to a respective one of the analyzer crystals.

99. The system of claim 95 wherein the monochromator crystals are symmetric crystals.

100. The system of claim 99 wherein the monochromator crystals are silicon crystals.

101. The system of claim 100 wherein the silicon crystals have [333] reflection.

102. The system of claim 95 wherein the analyzer crystals are Bragg type crystals.

103. The system of claim 95 wherein the object is a soft tissue object.

104. The system of claim 103 wherein the soft tissue object is breast tissue.

105. The system of claim 95 wherein the third X-ray beams apply a total radiation dosage of less than or equal to about 0.5 mrad to the object.

106. The system of claim 95 wherein the image detector is configured to receive the diffracted beams.

107. The system of claim 106 wherein the image detector is configured to produce a digitized image of the object.

108. The system of claim 106 wherein the image detector is a radiographic film.

109. The system of claim 106 wherein the image detector is an image plate.

110. The system of claim 95 wherein the image detector is configured to detect the image of the object from the beam diffracted from the analyzer crystals one of at or near a peak of a rocking curve of the analyzer crystal.

111. The system of claim 110 further comprising a computer configured to derive at least one of a diffraction enhanced image, an absorption image, a refraction image, a scatter image, and a mass density image of the object from the detected image.

112. The system of claim 110 wherein the one of at and near the peaks occurs approximately one-half of a Darwin width of the rocking curve.

113. The system of claim 95 wherein the image detector is configured to:
   detect a first angle image of the object from first diffracted beams emitted from the analyzer crystals positioned at first angular positions; and
   detect a second angle image of the object from second diffracted beams emitted from the analyzer crystals positioned at second angular positions; and wherein the system further comprises a computer configured to:
   combine the first and second angle images to derive a refraction and apparent absorption image; and
   derive a mass density image of the object from the refraction image.

114. The system of claim 113 wherein the image detector is configured to detect the first angle image of the object from the analyzer crystals at a low rocking curve angle setting of the analyzer crystals, and wherein the image detector is configured to detect the second angle image comprises detecting the second angle image of the object from the analyzer crystals at a high rocking curve angle setting of the analyzer crystals.

115. The system of claim 95 wherein the monochromator crystals are spaced apart from each other.

116. The system of claim 115 wherein the monochromator crystals are substantially linearly arranged, and wherein the spacing of adjacent monochromator crystals is substantially equal.

117. The system of claim 116 wherein the spacing of adjacent monochromator crystals is 0.5 cm to 25 cm.

118. The system of claim 95 wherein the second sides of the monochromator crystals are positioned such that the third X-ray beams are directed along paths substantially parallel to paths of the first X-ray beams.

119. The system of claim 95 wherein the monochromator crystals are one of germanium and silicon monochromator crystals.

120. The system of claim 95 wherein the monochromator crystals are one of germanium [333] and silicon [333] monochromator crystals.

121. The system of claim 95 comprising a computer configured for adjusting a radiation dose applied by the third X-ray beams to the object.

122. The system of claim 95 wherein the first side opposes the second side on a same monochromator crystal.

123. The system of claim 122 wherein the first side of the monochromator crystals faces the second side of adjacent monochromator crystals.

* * * * *